United States Patent
Fritsch et al.

(10) Patent No.: US 6,887,714 B2
(45) Date of Patent: May 3, 2005

(54) MICROVOLUME IMMUNOABSORBANT ASSAYS WITH AMPLIFIED ELECTROCHEMICAL DETECTION

(75) Inventors: Ingrid Fritsch, Fayetteville, AR (US); Robert Beittle, Jr., Fayetteville, AR (US)

(73) Assignee: Board of Trustees of the University of Arkansas, N.A., Little Rock, AK (US)

(*) Notice: Subject to any disclaimer, the term of this patent is extended or adjusted under 35 U.S.C. 154(b) by 247 days.

(21) Appl. No.: 09/978,734

(22) Filed: Oct. 15, 2001

(65) Prior Publication Data

US 2002/0058279 A1 May 16, 2002

Related U.S. Application Data

(60) Provisional application No. 60/240,691, filed on Oct. 16, 2000.

(51) Int. Cl.[7] .............................................. G01N 33/543
(52) U.S. Cl. ..................... 436/518; 436/514; 436/540; 435/4; 435/7.1; 435/7.8; 204/400
(58) Field of Search ................... 436/518, 514, 436/540, 523, 524, 525, 535; 435/4, 5, 6, 7.1, 7.2, 7.21, 7.22, 7.32, 7.4, 7.6, 7.72, 7.8, 7.9, 7.91, 7.92, 7.93, 7.94, 7.95, 287.3, 289.1, 7.5, 7.7, 7.71; 422/50; 204/400, 403

(56) References Cited

U.S. PATENT DOCUMENTS

| 4,779,031 A | 10/1988 | Arends et al. ............... 318/565 |
| 4,891,242 A | 1/1990 | Ito et al. .................... 427/53.1 |
| 4,961,806 A | 10/1990 | Gerrie et al. ............... 156/252 |

(Continued)

OTHER PUBLICATIONS

Stock Product Catalog 501, Baldor Motors and Drives, Jan. 1, 1997.
The Animatics SmartMotor, Animatics Corporation.
Industrial electronics, Technology 1998 Analysis & Forecast, IEEE Spectrum, Jan. 1998, p. 73–78.
Craig D.T. Bratten, Peter H. Cobbold, Jonathan M. Cooper; Micromachining Sensors for Electrochemical Measurement in Subnanoliter Volumes; *Anal. Chem.*, 1997, vol. 69 No. 2, Jan. 15, 1997, pp. 253–258.
K. Leyendecker, W. Bacher, W. Stark, A. Thommes; New Microelectrodes For the Investigation Of the Electroforming Of Liga Microstructures; *Electrochimica Acta*, 1994, vol. 39, No. 8/9, pp. 1139–1143.
Osamu Niwa, Masao Morita, Hisao Tabei; Fabrication and characteristics of vertically separated interdigitated aray electrodes; *J. Electroanal. Chem.*, 1989, 267, pp. 291–297.
Alan M. Bond, Darryl Luscombe, Keith B. Oldham, Cynthia G. Zoski; A Comparison Of the Chronoamperometric Response At Inlaid and Recessed Disc Microelectrodes; *J. Electroanal. Chem.*, 1988, 249, pp. 1–14.

(Continued)

*Primary Examiner*—Christopher L. Chin
*Assistant Examiner*—Ann Y Lam
(74) *Attorney, Agent, or Firm*—Head, Johnson & Kachigian

(57) ABSTRACT

A structure and method for chemical sensing utilizing microassays. Microcavities or micropores are combined with assay techniques to provide a very fast and very sensitive means of detecting chemical compounds. Assay techniques are modified to include a metal ion binding carrier species especially suitable for use in conjunction with the electrochemical detection. This allows assays to be combined with electrochemical analysis, thus allowing the high speed ease and hypersensitivity available in the invention disclosed herein.

7 Claims, 16 Drawing Sheets

U.S. PATENT DOCUMENTS

| | | | |
|---|---|---|---|
| 4,972,470 A | 11/1990 | Farago | 380/3 |
| 5,053,920 A | 10/1991 | Staffiere et al. | 361/383 |
| 5,149,630 A * | 9/1992 | Forrest et al. | 205/777.5 |
| 5,159,427 A | 10/1992 | Ogura et al. | 357/48 |
| 5,253,156 A | 10/1993 | Sakurai et al. | 363/98 |
| 5,313,150 A | 5/1994 | Arakawa et al. | 318/768 |
| 5,355,301 A | 10/1994 | Saito et al. | 363/147 |
| 5,365,405 A | 11/1994 | Hoenlein et al. | 361/766 |
| 5,384,691 A | 1/1995 | Neugebauer et al. | 361/794 |
| 5,410,107 A | 4/1995 | Schaper | 174/255 |
| 5,412,558 A | 5/1995 | Sakurai et al. | 363/98 |
| 5,413,939 A * | 5/1995 | Gustafson et al. | 436/518 |
| 5,432,675 A | 7/1995 | Sorimachi et al. | 361/719 |
| 5,434,745 A | 7/1995 | Shokrgozar et al. | 361/735 |
| 5,452,182 A | 9/1995 | Eichelberger et al. | 361/749 |
| 5,488,542 A | 1/1996 | Ito | 361/793 |
| 5,495,394 A | 2/1996 | Kornfeld et al. | 361/764 |
| 5,532,512 A | 7/1996 | Fillion et al. | 257/686 |
| 5,544,017 A | 8/1996 | Beilin et al. | 361/790 |
| 5,604,383 A | 2/1997 | Matsuzaki | 257/778 |
| 5,608,192 A | 3/1997 | Moriizumi et al. | 174/255 |
| 5,608,617 A | 3/1997 | Morrison et al. | 363/147 |
| 5,616,888 A | 4/1997 | McLaughlin et al. | 174/260 |
| 5,619,108 A | 4/1997 | Komurasaki et al. | 318/140 |
| 5,629,559 A | 5/1997 | Miyahara | 257/666 |
| 5,629,574 A | 5/1997 | Cognetti et al. | 310/71 |
| 5,634,267 A | 6/1997 | Farnworth et al. | 29/840 |
| 5,641,944 A | 6/1997 | Wieloch et al. | 174/252 |
| 5,753,517 A * | 5/1998 | Brooks et al. | 436/514 |
| 5,958,791 A * | 9/1999 | Roberts et al. | 436/514 |
| 6,066,448 A * | 5/2000 | Wohlstadter et al. | 435/6 |
| 6,090,933 A * | 7/2000 | Kayyem et al. | 536/25.3 |
| 6,391,624 B1 * | 5/2002 | Megerle | 435/287.2 |
| 6,485,983 B1 * | 11/2002 | Lu et al. | 436/514 |
| 6,740,518 B1 * | 5/2004 | Duong et al. | 435/287.2 |

OTHER PUBLICATIONS

Thor D. Osborn, Paul Yager; Formation of Planar Solvent–Free Phospholipid Bilayers by Langmuir–Blodgett Transfer of Monolayers to Micromachined Apertures in Silicon; *Langmuir*, 1995, 11, pp. 8–12.

Rose A. Clark, Paula Beyer Hietpas, Andrew G. Ewing; Electrochemical Analysis in Picoliter Microvials; *Anal. Chem.*, 1997, 69, pp. 259–263.

K.C. Burgers, K.J. Olejniczak, S.S. Ang, E. Porter; The Use of Multichip Module Technology for Power Electronics Miniaturization and Packaging; Department of Electrical Engineering, University of Arkansas; High Density Electronics Center (HiDEC), University of Arkansas, *Abstract*, 1997, pp. 35–41.

\* cited by examiner

Cross section of a pore in the polyimide film showing the funnel shape and film thickness Side of polyimide film where the laser entered, 60° tilt shows inside walls of the pore Side of polyimide film where the laser exited the film Shows the spacing between each pore

Flow chart of fabrication procedure

MICROVOLUME IMMUNOABSORBANT ASSAYS WITH AMPLIFIED ELECTROCHEMICAL DETECTION

CROSS-REFERENCE TO RELATED APPLICATIONS

This application is a continuation-in-part of U.S. provisional patent application No. 60/240,691 filed Oct. 16, 2000.

BACKGROUND OF THE INVENTION

1. Field of the Invention

The present invention relates to an ultra small scale chemical detection system. More specifically the present invention relates to microstructures used in conjunction with chemical assays. The microstructures are combined with known assay methodologies as well as assays that have been developed to be specifically adaptable for use with microcavities and micropores. The microstructures may be located on either rigid or flexible substrates.

2. Prior Art

There is a great need to miniaturize the analytical methodologies and instrumentation for making rapid and sensitive analyses in biological, environmental, medical and food applications. The interest in decreasing the analysis volume is of value for samples which are precious, expensive, require high spatial chemical resolution, and need improved throughput (e.g. more sample capacity in a smaller space). This does not necessarily demand better detection limits. However, improvements in limits of detection increase sensitivity and accuracy and are also beneficial for dilute analyte in small samples.

One analytical methodology that has been successful at providing the high specificity and selectivity, and which is transferable to small volumes is the immunoassay. This approach has been primarily designed for medical diagnostics, and combines the highly specific antigen (Ag) antibody (Ab) interaction with the sensitivity of the transducer system that may be optical, piezoelectric or electrochemical. Immunoassays with electrochemical detection are desirable for a wider range of uses because highly specific and precise current measurements can be performed with simple instrumentation, using opaque device materials, and in colored and turbid samples minimizing prior pre-treatment procedures.

Some of the smallest analyzed volumes have been reported for homogeneous immunoassays, although with poorer detection limits than those reported here for a heterogeneous assay. One type of small homogeneous assay involves laser induced fluorescence detection combined with fast separation of bound and unbound antibody-antigen complexes in microfluidic systems. Another has the advantages of the simpler electrochemical detection and can be performed in a drop (600 pL) under mineral oil in a microcavity. The latter device, however, does not include a separation step, and therefore may be susceptible to interferences from other sample species. Heterogeneous assays have the advantage that the analyte is concentrated via immobilization on a chemically-selective surface, which enhances detection limits, while unreacted species are separated by washing steps.

Recently, an example of an electrokinetically-driven microfluidic chip for heterogeneous bioassays using about 118 nL volume and assay times below 5 min was reported. Detection was performed with laser induced fluorescence. Complications include modifying the walls of the channel, which affects the electro osmotic flow, and elution of fluorescent-labeled-immobilized species to bring them to the detection site. Low detection limits (pg/mL or fM) have not yet been demonstrated.

Detection immediately adjacent to the surface-immobilized immuno components should supply the largest signals with the shortest incubation periods. This has been accomplished with scanning electrochemical microscopy (SECM). Detection limits as low as 5.25 pg/mL have been obtained. However, long total assay times have been reported (1 h and up). Only the sample volume is small (10 is of pL36 up to several $\mu$L) which is spotted onto a surface (and dried, followed by rinsing) or immobilized onto magnetic immuno beads first, which are subsequently transferred to a surface for electrochemical detection. Yet, the enzymatic generation of electrochemically-detected species is carried out on large volumes that must keep both the SECM electrode and the auxiliary/reference electrodes in electrochemical contact. Consequently, this setup is not well-suited for integration with small volume handling or automation and has added complexity due to the SECM instrumentation and operation.

Wang et al. reported a heterogeneous immunoassay for human serum albumin on a thick-film electrochemical device. The immuno components are also immobilized adjacent to the detecting electrode and small volumes may be used at all stages of the immunoassays. However, unlike our system, the immuno components are attached in a noncovalent fashion to all surfaces (instead of selected ones), the overall dimensions are large (several millimeters) and therefore, the volumes must be larger (30 $\mu$L) to cover electrodes and modified surfaces, the area of the immuno active surface exposed to solution is less well defined because it depends upon the size of the drop and wetting properties of the substrate, and the detection (based upon potentiometric stripping analysis) yields detection limits that are higher (0.2 $\mu$g/mL).

The general immunoassays procedure for it is based on that described by Heineman and coworkers. This involves immobilization of the primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine) which is electrochemically reversible at potentials that do not interfere with reduction of oxygen and water at pH 9.0, where AP exhibits optimum activity. In addition, $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 $\mu$l to 360 $\mu$L have been reported previously. In a capillary immunoassays with electrochemical detection, the lowest detection limit reported thus far is 3000 molecules of mouse IgG using a volume of 70 $\mu$L and a 30 min or 25 min assay time. Those skilled in the art will recognize the above described assay as a sandwich-type immunoassay and will appreciate that this is only one of many immunoassays. Alternatives include competitive binding immunoassays and immunoassays utilizing a more general physisorbing material other than a primary antibody.

Immuno assays are only one category of a very wide variety of surface immobilization chemical detection assays. Northern and southern blot assays are well known techniques for detecting specific polynucleotide sequences. They involve surface immobilization of polynucleotides. Surfaces having one or more lipid layers may be used to immobilize and detect compounds having hydrophobic regions. Molecular interactions may also be taken advantage of to develop surface immobilization chemical detection assays. When two molecules are known to bind to one another, one may be covalently attached to a substraight. The substraight is then exposed to a sample such that the other interacting molecule is given an opportunity to bind to the substrate bound molecule. The substrate is then rinsed leaving only bound analyte on the substrate. A number of detecting methods may then be applied to the surface. Detecting methods include using secondary antibodies as described above, detecting the bi-products of an enzymatic reaction characteristic of the analyte, spectroscopy, flourescents, electrochemical analysis or other methods known to those skilled in the art.

These assays generally require a laboratory setting. A person wishing to analyze a sample with one of the above described assays most usually send the sample to a laboratory. Even while in a laboratory, many chemical detection assays take a relatively long period of time.

It is therefore desirable to provide a method for rapid chemical detection.

It is also desirable to provide a highly sensitive for detecting low amounts of analyte in a very small amount of sample.

It is also desirable to provide a method for detecting an analyte in a small sample having very high accuracy.

SUMMARY OF THE INVENTION

In the present invention, the term microstructures refers to both microcavities and micropores. These microstructures are formed by using chemical and/or physical etching processes in combination with thermal evaporation and other layering techniques. Alternating layers of insulating and conducting materials are applied to either a solid or flexible substrate. The substrate may have pre-formed holes in order to form pores or may have holes drilled through them after the formation of cavities in order to form pores. The alternating conducting layers serve as electrodes. How deep the wells or pores are, depends on how many layers are applied to the initial substrate.

The methods used to form these microstructures allow them to be extremely small. Micropores and microcavities may be formed that are less than a hundred micrometers wide. In fact they may be less than 10 $\mu$m wide. The depth of the microstructures ranges anywhere from less than 10 $\mu$m to over 100 $\mu$m. In the present invention, the microstructures described above are combined with known chemical detection assays. Surface immobilization assays are especially well suited for these micro structures, although any assays susceptible to electrochemical detection may be combined with these microstructures. Surface immobilization assays are well known to those skilled in the art and include, but are not limited to, immunoassays, northern and southern blots, western blots and incorporation of proteins into lipid layers. Surface immobilization assays are especially advantageous for use in microstructures because the small size of the structures allows for a very short distance between the analyte being detected and the electrodes being used for electrochemical detection. In addition, the short distance between the electrodes used for detecting the analyte also accelerates both detection and amplification by means of redox cycling. Another benefit of combining surface immobilization assays with electrochemical microstructures is that physisorption of materials used for surface immobilization may be regulated within the microstructure. By applying electrical currents to various electrodes, the location of analyte binding materials within the microstructure may be controlled. This allows a certain material, such as protein binding styrene or primary antibodies, to bind to insulating layers or specific electrodes while preventing phsysiabsorption of these molecules to working electrodes.

These microstructures having surface immobilization assays incorporated within them may be further modified by the formation of a lipid bi-layer. Organic compounds may be used to anchor a lipid bi-layer to the rim of a microcavity or, alternatively, to one or both openings of a micropore.

A self-contained, microelectrochemical heterogeneous immunosensor on the smallest volumes reported to date (1 $\mu$L for the antigen, 1 $\mu$L for the secondary antibody-enzyme conjugate, and 200 nL for the electrochemically detected species) has been developed using mouse IgG as a model system in a sandwich type enzyme-linked immunosorbent assay (ELISA), which takes less than 30 min to both complete the assembly of immunoassay components onto the antibody-modified surface and detect enzymatically-generated species. These studies demonstrate the advantage of the close proximity of electrodes to modified surfaces and their application in the analysis of small volumes. Using a micro cavity with individually-addressable electrodes on a microfabricated chip, the primary antibody was selectively and covalently attached at a gold, recessed microdisk (RMD) at the bottom of the microcavity to the free end of SAMs of either 11-mercaptoundecanoic acid or 11-mercaptoundecanol using 1-ethyl-3-[3-dimethylaminopropyl]-carbodiimide hydrochloride. Non-specific adsorption to the surrounding material, polymide, of the microcavity device was eliminated. Electrochemical desorption was used to confine the immunoassays activity at the RMD. Alkaline phosphatase, which is conjugated to a secondary antibody is used for the enzymatic conversion of the substrate p-aminophenyl phosphate to p-aminophenol ($PAP_R$) and is detectable in less than 30 s using cyclic voltammetry at a gold, tubular nanoband electrode, which is on the wall of the microcavity and immediately adjacent to the modified RMD. A third electrode, also within the region of the microcavity, served as the counter/reference electrode. Calibration curves were obtained for 1 $\mu$L solutions of 5 ng/mL to 100 ng/mL of IgG and for 200 nL solutions of 5 mM to 4 mM of $PAP_R$. Detection of 4.4 nM (6.4 ng/mL) or 880 fmol (129 pg) for $PAP_R$ and 56 fM (9 pg/ml) or 56 zmol (9 fg) for IgG has been achieved The device is suitable for analysis with volumes down to 10 pL.

The self-contained, microelectrochemical enzyme-linked immunosorbent assay (ELISA) device that we report here has the advantages of the SECM systems, but is better suited for small volumes, miniaturization, and for integration with microfluidics (to improve ultra small volume sample handling and speed). The basic design is a microcavity. Each microcavity possesses three, individually addressable electrodes as integral components, making them excellent candidates for self-contained analysis in small volumes. Thus, unlike electrochemical immunoassay techniques previously reported, the self-contained electrochemistry in our system eliminates the need for an external reference and auxiliary electrode. FIG. 1 shows a top-down view of a microcavity chip, which consists of alternating layers of gold (with a chromium adhesion layer) and polymide (an insulator)

deposited and patterned on an oxidized silicon substrate. One of the electrodes is a recessed microdisk (RMD) electrode at the bottom of the cavity, a second, which is 4 μm away from the RMD, serves as a tubular nanoband (TNB) electrode along the inner wall, and the third (top layer), which is 4 μm away from the TNB and 8 μm away from the RMD, accesses the rim and top surface surrounding the cavity. Connections to the electrodes in each cavity are made through an edge connector. All of the work described here was performed on microcavities that are 50 μm in diameter and 8 μm deep (geometric volume is 16 pL). There is one microcavity of this size present on each chip.

The ELISA components may be immobilized on the RMD while the nearby TNB (working electrode) and top layer (pseudoreference/auxiliary electrode) perform the electrochemical detection. The actual magnitude of the electrochemical signal depends upon geometry and dimensions of the device, electrode, and immunoassay-modified surface. Because all electrodes are contained in the same small space, ultra small volumes are possible at all stages of the immunoassays. In addition, these devices offer the possibility of further redox cycling (leading to signal amplification) between detecting electrode and other electrodes. The fixed, close proximity between detector and modified surface makes low detection limits possible and reproducible, and does not require micromanipulators. The response is fast because of the short distance for enzymatically generated species to diffuse from the RMD to the TNB. Finally, separation of the modified surface from the detecting electrode has advantages over traditional electrochemical sensors where detecting electrodes are also the ones that are modified: (1) the stability of the modified surface is improved because there are no electron transfer events through or changes in potential in that layer, and (2) it allows for a large electrochemical signal because the detecting electrode is bare.

Mouse IgG was chosen as the model analyte for our system. We demonstrate performance on the smallest sample volume (without a second transfer step or drying) and provide the lowest detection limits for $PAP_R$ to-date for heterogeneous electrochemical immunoassays.

Initial surface modification of immuno components on gold macro substrates and physisorption to polymide macro substrates were studied first, before implementing immunoassays in the microcavities. The Ab is immobilized through covalent attachment to self-assembled monolayers (SAMs) of either 11-mercaptoundecanoic acid (MUA) or 11-mercaptoundecanol (MUOL) at the surface of the RMD using 1-ethyl-3-[3-(dimethylaminopropyl)]-carbodiimide hydrochloride (EDC). The use of the long alkyl chain thiols, MUA and MUOL, for the mouse IgG immunoassays is new. Long chain thiols were chosen because it has been reported that they show more surface stability than short chain thiols. Because electrochemical detection was not performed by the electrode underlying the modified surface, the total thickness of the modifying layer, which would otherwise limit the signal, was not a concern. This approach provides significant advantages over existing electrical biosensors. The surface characterization was performed by polarization modulation Fourier transform infrared spectroscopy (PM-FTIR). Activity was evaluated by exposing modified macro substrates to a PAPP solution, followed by cyclic voltammetry (CV) detection of $PAP_R$ at a separate bare macroelectrode.

The knowledge gained about surface modification and activity from the macro scale studies was then applied toward converting microcavities to microspace immunosensors. The procedure that is used eliminates physisorption to the polymide portions of the device, isolates the immunoassays activity to the RMD, and minimizes the fouling of the TNB and top layer. Calibration curves for both IgG and PAPR were obtained and detection limits were determined for the microelectrochemical immunoassays, which involves 1 μL volumes for each step, and as little as 200 nL for the last step (the PAPP solution). This work is not only important to the development of individual chemical sensors for small volumes, but also for arrays of sensors, where localized modification of different immunoassay components and the elimination of undesirable physisorption are essential.

While standard sandwich-type ELISA's such as the one described above are very useful because they are ubiquitous in the art of chemical detection, other immunoassay methods are also suitable for use inside microcavities. Those skilled in the art will recognize that there are a variety of immunoassay methods. Immunoassays may be used not only in sandwich-assays as described above, but also competitive binding assays. Similarly, the primary antibody may be replaced with a variety of chemical compounds. If the analyte is a polynucleotide, it may be desirable to use cDNA in place of the antibody. The analyte anneal 5 to the cDNA inside the microcavity and the secondary antibody will then bind to the polynucleotide analyte. It is also known to utilize compounds that bind to proteins, lipids, carbohydrates, bacteria or viri in place of the primary antibody. Although using general compounds that bind to more general types of molecules will eliminate the specificity provided by the primary antibody, the specificity of the overall immunoassay is preserved by use of the secondary antibody. Those skilled in the art will recognize that it is common practice to utilize compounds other than the primary antibody for binding of the analyte to the assay substrate.

In the present invention, a new immunoassay method has been developed that is especially well suited for use in conjunction with microcavities. The above described methods of utilizing primary antibodies or other compounds to bind the analyte to substrate may all be used in this newly developed immuno assay. The improvement to immunoassay technology in the present invention lies in the modification made to the secondary antibody. Immunoassays usually are enzyme-linked, thus providing the first 2 letters of the acronym ELISA. The secondary antibody is linked to a catalytic protein, usually by either splicing the protein and antibody genes together or by conjugation them in a chemical reaction. These enzymes conjugated to the secondary antibody react with their substrate to form a product which may then be detected. In the method described above, an enzyme converts $PAP_O$ to $PAP_r$. PAP then cycles between electrodes changing back and forth between the oxidized and reduced state. This causes the voltametric signal to be amplified. The present invention includes the development of utilizing metal ion releasing compounds attached to the secondary anti-body in place of an enzyme. The released metal ion then may be directly detected by the electrodes within the microcavity. Utilizing a metal releasing compound, such as a metal protein, provides a more reliable and more accurate immunoassay when used in conjunction with a microcavity.

The general concept of the microelectrochemical device described here has many advantages for use in chemical sensing. The use of a layering fabrication method allows electrodes to be constructed within short distances of each other and yet remain individually addressable. This permits analysis of very small volumes. In addition, controlling an electrode's potential provides selective surface modification (either by adsorption or desorption). Therefore, immunoassays components are located closely to other electrodes so that detection occurs not only separately from the modified surface, but also rapidly in a concentrated region of enzymatically-generated products, resulting in excellent stability, high signal, and short response time.

We have demonstrated the utility of the features of this device in a microelectrochemical immunoassays for IgG. The results illustrate the promise of miniaturized electrochemical systems for complex chemical analysis of ultra small samples. This invention makes smaller volumes are no more difficult to analyze than macrovolumes because all of the electrodes are prefabricated within the same small volume, thereby allowing self-contained electrochemistry to occur. We have shown that in fact, not only can a heterogeneous immunoassays in such electrochemical systems be applied to smaller sample volumes than reported previously, but they also offer better detection limits, sensitivity, and speed because of the close proximity of electrodes and modified surfaces. In addition, we have developed a new polymide passivation protocol that protects the detecting electrodes until they are needed and prevents immuno active physisorption to undesirable locations. These procedures allow fabrication of accurate and reliable immunosensor arrays. This procedure is also promising for modification in enclosed microfluidic devices where photo patterning may not be convenient.

DETAILED DESCRIPTION OF THE PREFERRED EMBODIMENTS

One of the significant advantages of the chemical sensing device disclosed herein is the fact that it makes use of microcavities and micropores. The small size of these microstructures, less than a hundred micrometers in diameter, results in the electrodes being very close to one another. The short distance between electrodes greatly increases both the speed at which sensing occurs and the sensitivity of the device. Alternate layers of insulator and electrode are applied to a substrate. The substrate may be either rigid as when a silica chip is used or flexible, as when a polyimide film is used. Chemical etching processes are used to etch a pattern into the alternating layers of conductor and insulator as they are applied to the substrate see FIG. 6. Those skilled in the art will recognize chemical etching as a common process. The process of forming microstructures on rigid silica wafers is described in the detail in example.

Figure 1:
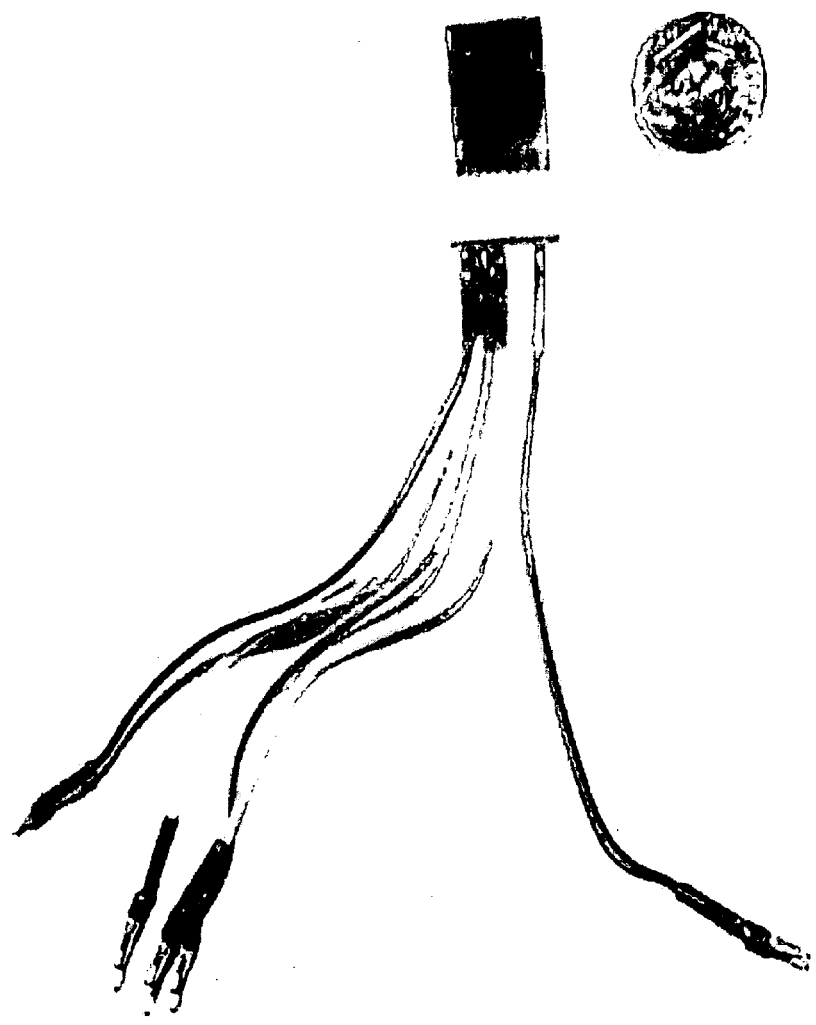
FIG. 1. The microcavity chip design contains 4 microcavities with diameters ranging from 2 $\mu$m to 50 $\mu$m. The leads shown are used to access the individually addressable electrodes in the 10 m and 50 $\mu$m cavities. Photograph of a microcavity device inserted into an edge connector with which contact is made to the potentiostat. The top layer of gold can be clearly seen and can be addressed by an alligator clip. The microcavities, which cannot be resolved in this photograph, reside along the top, free edge of the chip. The leads, on the opposite end, are used to access the individually addressable RMD and TNB electrodes in the 10 m and 50 m cavities.
Figure 2:
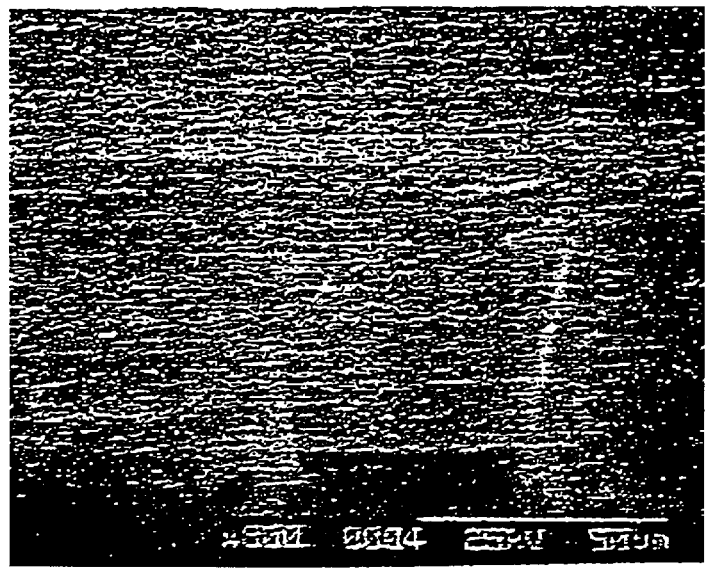
FIG. 2. Shows a cross section of a pore in a polyimide film.
Figure 3:
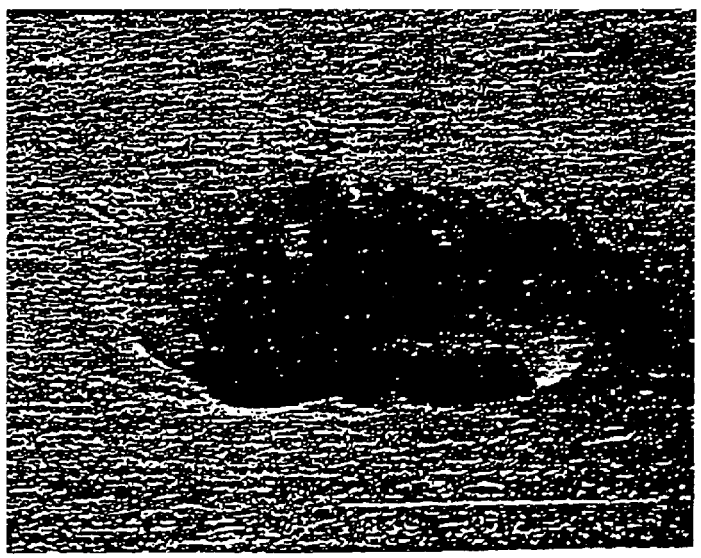
FIG. 3. Shows a micropore in a polyimide film from the side on which the laser entered.
Figure 4:
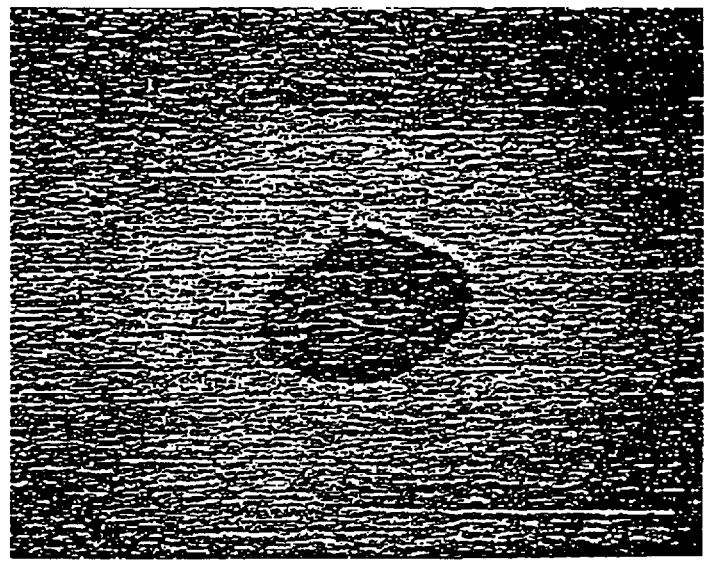
FIG. 4. Shows a pore in a polyimide film from the side from which the laser exited.
Figure 5:
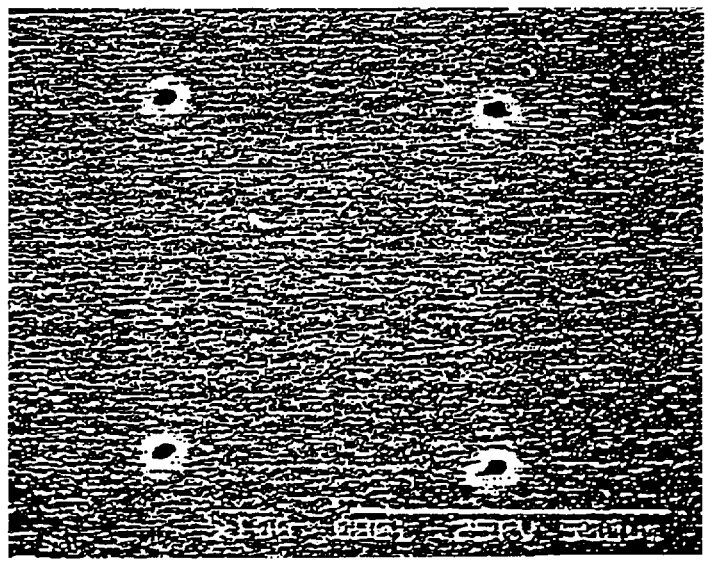
FIG. 5. Shows an array of micropores on a polyimide film.

Formation of microstructures on flexible polyimide films involves essentially the same process. When desiring to form micropores on a flexible polyimide film, it is often desirable to form a pore in the film prior to the layering and etching process. Pores in the polyimide film are formed by an excimer laser. As the laser passes through the film, it slowly disperses and the resulting pore has a funnel shape. FIGS. 2, 3 and 5 are electron micrographs showing a pore through a polyimide film resulting from application of an excimer laser. The average diameter of the pore where the laser enters the film is 70 mm, shown in FIG. 3. The average diameter where the laser exits the film is 30 mm, shown in FIG. 4.

Figure 6:
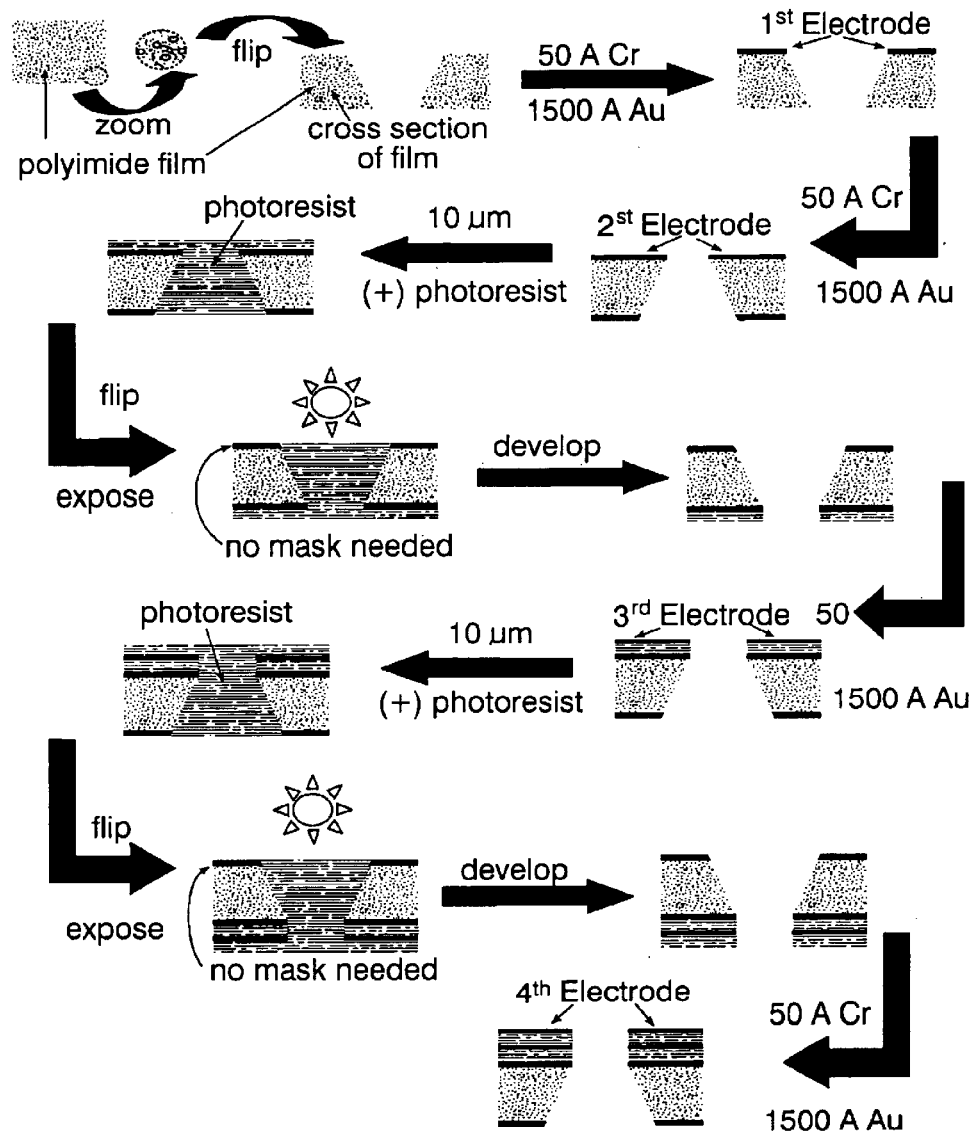
FIG. 6. Shows a flow chart of the fabrication procedure utilized to form electrodes in a micropore on a polyimide film.

A flow chart for the fabrication procedure is shown in FIG. 6. The polyimide film was cut to a workable size, put into a carrier to pattern the gold layer, and placed at a vertical angle in the thermal evaporator to reduce the chances of shorting between gold layers. A 50 angstrom chromium film is applied to the polyimide film by thermal evaporation in order to form an adhesion layer. Next, a 1,500 angstrom gold film was deposited also by thermal evaporation. The process is then repeated on the opposite side of the film.

When forming a microstructure around a pore in a polyimide film, the photoresist from the etching process is itself used as the insulating layer. A 10 micrometer thick positive photo resist film is applied to the polyimide film. When the positive photoresist is exposed to UV light, it washes away in developer solution. If the photoresist is covered to block the UV light, it will not develop away in the solution. After application of the photoresist to both sides of the film, one side is exposed to UV light. This way, only the photoresist on the side facing the UV light and the photoresist within the pore itself develop away in solution. This leaves an insulating layer on the side of the film facing away from the UV light source. Thermal evaporation is used to apply a subsequent conducting layer to the side having photoresist insulator. This process is repeated to form as many alternating conducting and insulating layers as is desired.

Whether a cavity or pore is more desirable will depend on the environment into which the microstructure is to be used. Similarly, whether a rigid or flexible microstructure is formed will also depend on the purpose to which the microstructure is to be used. Pores may prove more desirable in devices that use flow through analysis. They may prove especially suitable for microfluidic devices. Flexible micropores and microcavities may prove more suitable in medical or biological testing applications.

Figure 7:
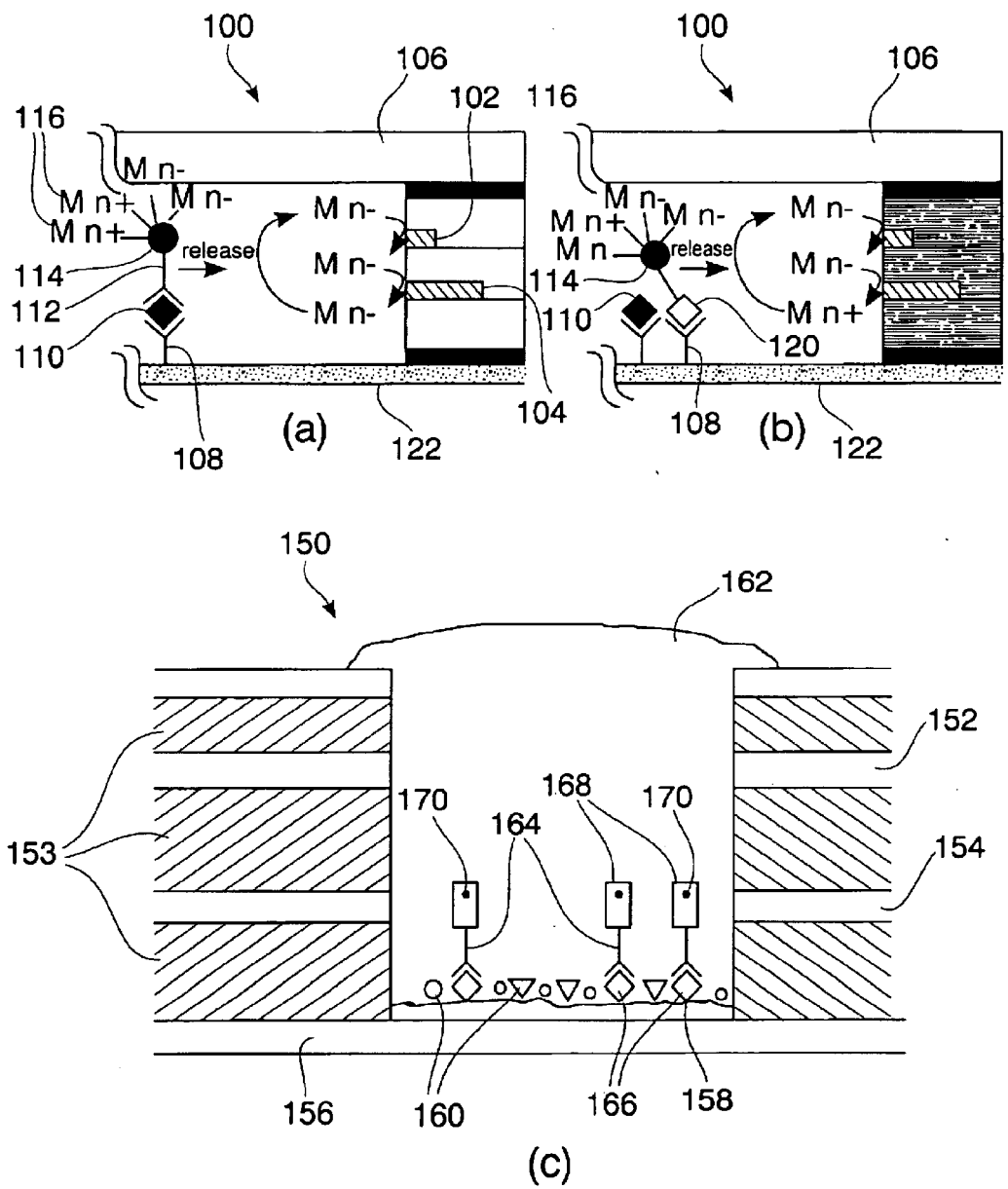
FIG. 7A. Shows a schematic diagram of a microcavity being used in conjunction with a sandwich type immunoassay.
FIG. 7B. Shows a schematic diagram of a microcavity being used in conjunction with a competitive binding immunoassay.
FIG. 7C shows a schematic diagram of a microcavity being used in conjunction with an immunoassay utilizing a protein adhesion layer instead of a primary antibody.

While standard sandwich-type immunoassays are very useful because they are ubiquitous in the art of chemical detection, other immunoassay methods may be more suitable for use inside microcavities. Those skilled in the art will recognize that there are a variety of immunoassay methods. Immunoassays may be used not only in sandwich-assays as described above, but also competitive binding assays as shown in FIG. 7B. Similarly, the primary antibody may be replaced with a variety of chemical compounds. If the analyte is a polynucleotide, it may be desirable to use cDNA in place of the antibody. The analyte will then anneal to the cDNA inside the microcavity and the secondary antibody will then bind to the polynucleotide analyte. It is also known to utilize compounds that bind to proteins, lipids, carbohydrates, bacteria of viri in place of the primary antibody. Although using general compounds that bind to more general types of molecules will eliminate the specificity provided by the primary antibody, the specificity of the overall immuno assay is preserved by use of the secondary antibody. Those skilled in the art will recognize that it is common practice to utilize compounds other than the primary antibody for binding of the analyte to the assay substrate.

In the present invention, a new immuno assay method has been developed but is especially well suited for use in conjunction with microcavities. The above described methods of utilizing primary antibodies or other compounds to bind the analyte to substrate may all be used in this newly developed immunoassay. The improvement to immunoassay technology in the present invention lies in the modification made to the secondary antibody. Immunoassays normally are usually enzyme-linked, thus providing the first 2 letters of the acronym ELISA. The secondary antibody is linked to a catalytic protein, usually by splicing the protein and antibody genes together. These enzymes attached to the secondary anti-body react with their substrate to form a product which may then be detected.

In the method described above, the enzyme converts $PAP_0$ to $PAP_r$. The present invention includes the development of utilizing a metal ion releasing carrier species attached to the secondary anti-body in place of an enzyme. The released metal ion then may be directly detected by the electrodes within the microcavity. Utilizing a metallo releasing compound, such as a metal protein, provides a more reliable and more accurate immunoassay when used in conjunction with a micro cavity.

FIG. 7A shows the invention utilizing a sandwich-type immunoassay. Microcavity 100 has been formed upon a silica chip substrate 122. Electrodes 102 and 104 have been formed with insulating layers between them. Class slide 106 has been placed over the top of cavity 100 in order to prevent evaporation. Primary antibody 108 has been attached to substrate 122 on the bottom of microcavity 100. Analyte 110, the chemical compound being detected by the microcavity sensor, has bound to the primary antibody which is designed specifically for analyte 110. Secondary antibody 112 is covalently bound to carrier species 114. This is usually done by splicing the genes coating for secondary antibody 112 and carrier species 114 together and causing a host cell to express the recombinant gene as a single polypeptide. However, it is known in the art that there are a variety of less sophisticated organic methods of attaching carrier species to secondary antibodies. Metal ions 116 are attached to carrier species 114. In this particular embodiment, carrier species 114 is capable of holding several metal ions 116. The type of carrier species utilized will determine how many metal ions are attached to it.

Those skilled in the art will recognize that there are a variety of carrier species known to the field of biochemistry. These include metallthionin, ferritin, heme, dendrimer, and staph nuclease. Those skilled in the art will recognize that these are only a very few of the many polypeptides capable of binding to metal ions. When using one of these polypeptides as a carrier species it may be desirable to splice several copies of the carrier species gene to the end of the secondary antibody gene. This would form a polypeptide polymer tail on the secondary antibody and increase the number of metal ions for use in the microimmunoassay sensor.

Once the secondary antibody 112 has attached to analyte 110, the microcavity is treated so as to activate carrier species 114. Activation as stated previously may be comprised of changing temperature, changing ph, sending an electric charge through the microcavity, exposure to electromagnetic radiation, addition of a chelating agent or the addition of a compound that reacts with carrier species 114 so as to activate it. Once metal ions 116 are released from carrier species 114, they diffuse throughout the solution and begin to carry current between electrodes 102 and 104. The presence of the analyte is detected by the existence of a current through the microcavity. The extremely small size of the microcavities and the short distance between the electrodes means that even an extremely small amount of analyte may be detected by this microstructure.

FIG. 7B shows a microimmunoassay that is similar to that of FIG. 7A. Here, instead of a sandwich immunoassay, a competitive binding immunoassay is used in the microcavity. Primary antibodies 108 are attached to substrate 122 of the microcavity. Analyte 110 is then added to the microcavity and binds to primary antibody 108. Carrier species 114 is not bound to a secondary antibody, but rather to an analyte mimicking molecule 120. The analyte mimicking molecule 120 binds to primary antibody 108 just as analyte 110 does. The carrier species 114 is then activated so as to release metal ions 116 and induce current between the electrodes. While a sandwich microimmunoassay as shown in FIG. 7A indicates the presence of analyte by the existence of a current, the competitive binding assay shown in FIG. 7B indicates the presence of analyte by a lack of current between the electrodes.

FIG. 7C shows another type of immunoassay well suited for use in microcavities. The microcavity is built upon substrate 156 which may be either a solid silica substrate or a flexible polyimide substrate. Electrodes 152 and 154 are separated by insulating layers 153. In the body of microcavity 150 is a protein adhesive layer 158. Those skilled in the art will recognize that there are a variety of materials to which all polypeptides adhere. In this immunoassay, the sample is applied to the microcavity and analyte 166 binds to layer 158, as do other proteins 160. Secondary antibodies 164 are bound to carrier species 168 that each contain a metal ion 170. Secondary antibodies 164 bind to analyte 166. Carrier species 168 are then activated to release ions 170 that create a current between electrodes 152 and 154. This type of assay is similar to that found in FIG. 7A, except that the substance attached to the substrate binds several proteins and is not specific to one molecule as primary antibody 108 is.

Figure 8:
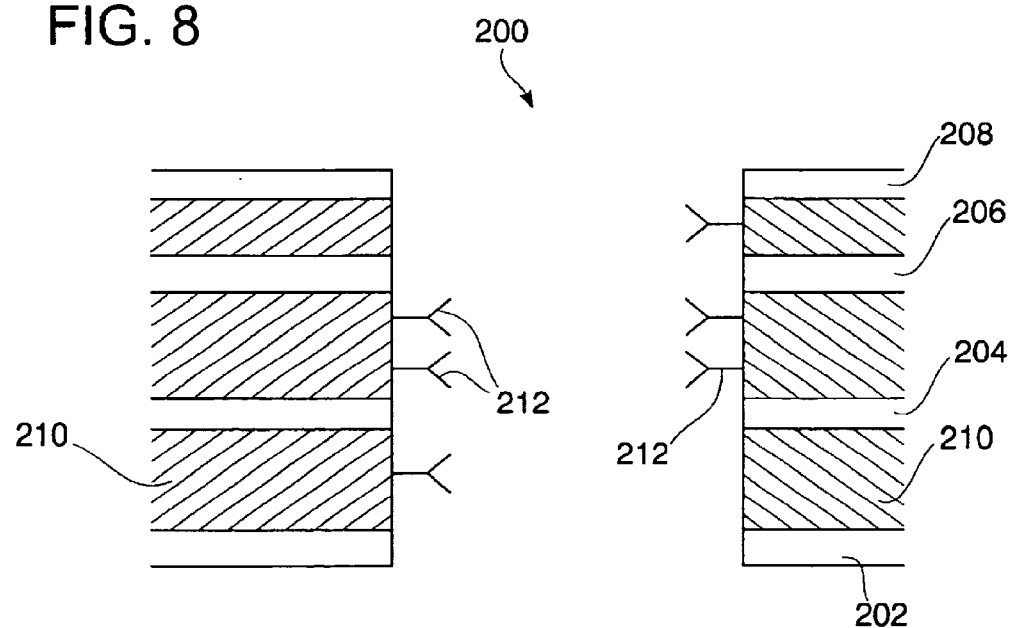
FIG. 8 shows a schematic diagram of a micropore being used in conjunction with a sandwich type imminoassay.

FIG. 8 shows microimmunoassay pore 200. Substrate 202 may be either a rigid silica wafer or a flexible polyimide film. Alternating layers of insulator 210 and electrodes 204 and 206 are applied according to the methods described herein. Final layer 208 is comprised of conductor material and provides stability to the microstructure. Primary antibodies 212 are attached to the insulating layers. The solution to be tested may be run either over or through pore 200. The immunoassay utilizes the same as that found in FIG. 7A, a sandwich immunoassay. Analyte binds to primary antibodies 212, secondary antibodies bind to analyte, and the carrier species attach to the secondary antibody is activated to release its ions and induce an electrical current. Those skilled in the art will realize that any of the immunoassays described herein are as suitable for use in micropores as they are for use in microcavities.

The immunoassays described in FIGS. 7A and 7B utilize a glass slide to cover the microcavity to prevent evaporation. As these microstructures are very small, evaporation becomes a serious consideration. It may therefore be desirable to cover the microcavity, thus preventing evaporation. It may also be desirable to suspend a film across the top of a microcavity or micropore. These films may serve as filters or may also be lipid blamers. Transport proteins may be inserted into lipid blamers and the analyte studied may be a transported compound. In this situation, the microsensing device described herein may be used to detect and measure the activity of various membrane transport proteins.

Figure 9:
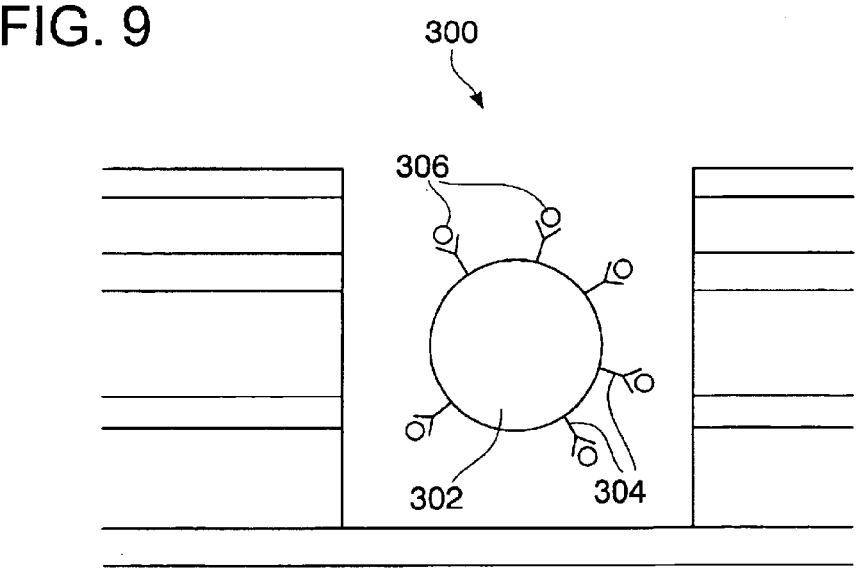
FIG. 9 shows a schematic diagram of a microimmunobead being used in conjunction with a microcavity.

FIG. 9 illustrates use of a microcavity in conjunction with an immunobead. Use of immunobeads allows the reaction of binding the analyte to the primary antibody to take place somewhere besides the microcavity. After the analyte has bound to the primary antibodies on the immunobead, the immunobead is then inserted into the microcavity and the immunoassay is carried out to completion as described above. Those skilled in the art will appreciate that immunobeads may be used either with sandwich or competitive binding immunoassays. Those skilled in the art will also realize that microbeads may be used in other types of assays.

In FIG. 9, immunobead 302 is covered in primary antibodies 304 which bind to analyte 306. Immunobead 302 is then inserted into microcavity 300. Microcavity 300 may be lined with material that faciltates physiabsorbtion of microbeads. Also, magnetic fields may be applied in order to coax microbeads into microcavities.

Figure 10:
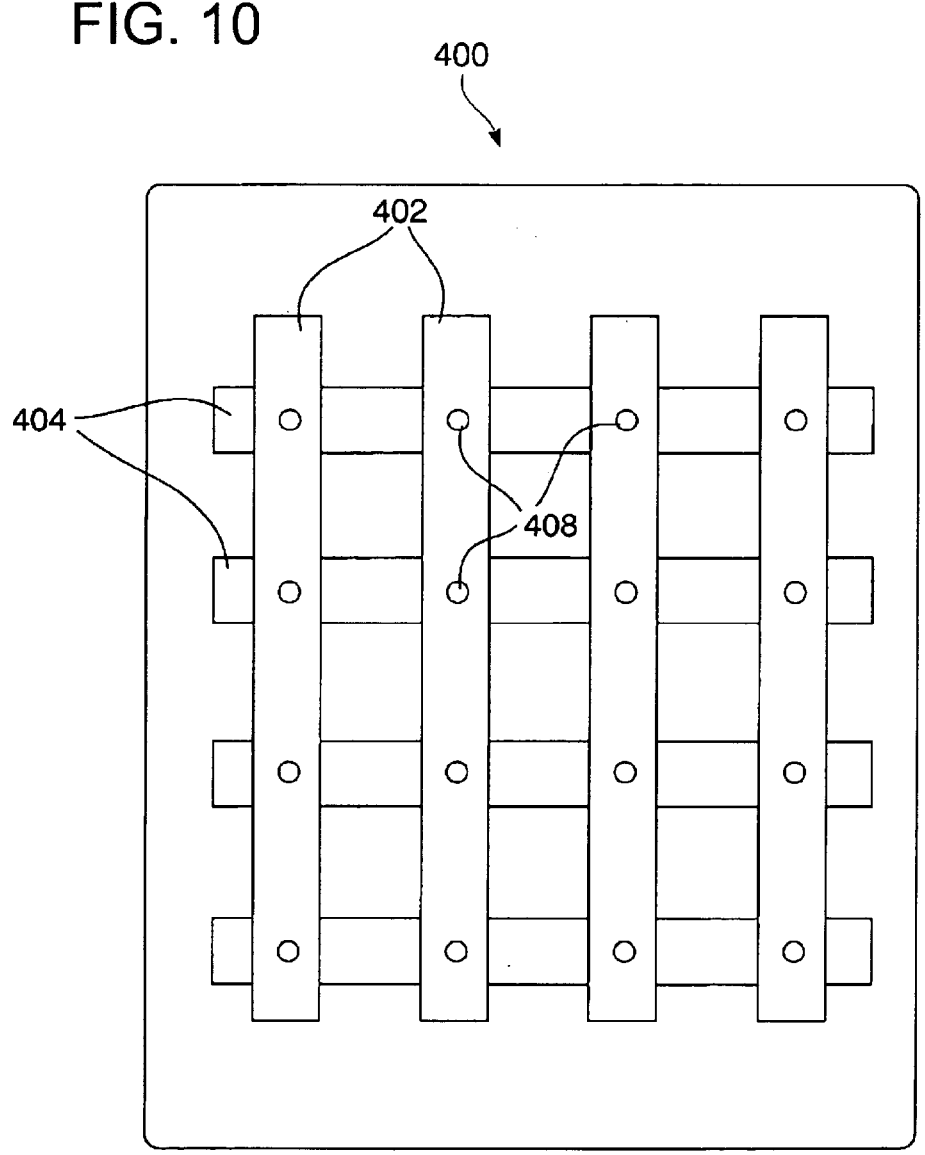
FIG. 10 shows a schematic diagram of an array of microcavities.

FIG. 10 illustrates an array of microcavities. Array 400 consists of several microcavities 408. Electrodes 402 are parallel to one another and contact multiple microcavities. Electrodes 404 are situated similarly to electrodes 402, but are perpendicular to electrodes 402. Electrodes 404 also contact multiple microcavities. Each microcavity may be designed to have a separate assay within it. Array 400 allows several analytes to be tested for simultaneously.

Those skilled in the art will recognize that there are a wide variety of both proteins and organic compounds capable of binding to metal ions. There are a number of well studied metallo proteins capable of binding to various metals such as iron, zinc, magnesium and copper to name a few. The genes that encode for these proteins may be spliced onto the end of the gene encoding for the secondary antibody genes in the same way that enzymes are spliced to secondary activating antibodies. After the secondary antibody binds to the analyte and the microcavity is rinsed, the metallo protein is treated so that it releases the metal ion incorporated within it. The metal ion attached to the metallo protein may be released in a variety of ways, depending on the protein used. Many metallo proteins release the incorporated metal ion upon a change in pH. This may be accomplished either by adding buffer to the solution or utilizing the electrodes within the microcavity themselves to release protons in the solution electrolitically. Other metallo proteins release their metal ions upon reaction with a secondary compound that may be added to the immuno assay subsequent to the rinsing step. Yet, other metallo proteins release their metal ions in the presence of chelating agents, such as ethylenediaminetetraacetic acid (EDTA). Those skilled in the art will recognize that these methods of coaxing metallo proteins to release their incorporated metal ions are well known to those skilled in the art. It will also be recognized to those skilled in the art that the addition of a metal releasing step involving pH adjustment or the addition of a compound may be incorporated into an immuno assay without any significant difficulty.

It may also be desirable to synthesize novel carrier species to attach to the secondary antibody. Those skilled in the art of protein engineering will recognize that there a number of common amino acid sequences capable of binding to metal ions. A Few examples are zinc fingers, cysteine loops, heme groups and the His $X_3$ His and His Pro Phe His sequences. These amino acid sequences may be added to existing, known polypeptides or may be incorporated into novel peptide sequences and spliced onto secondary antibodies. So long as the carrier species is capable of forming a stable bond with a metal ion and may be induced to release the metal ion by the addition of a compound, change in pH change in temperatures or other means easily adaptable for use with microcavity or micropore immunoassays, It will be suitable for use in this microelectro immunoassay.

One of the advantages of using a metal binding carries species is that it provides a metal ion that easily cycles between electrodes. This creates an automatic redox cycling reaction. Because of this, amplification is inherent to the assay. This eliminates the need for additional chemical amplification steps. Those skilled in the art will realize that this greatly simplifies chemical detection.

It is possible to use metal binding carriers species in conjunction with assays besides amino assays. For example, with Northern and Southern blots oligonucleotides may be bound to these carrier species. The blot assay may then be performed within a microcavity. This not only provides for very sensitive detection, it is much safer than standard Northern and Southern blots that utilize radioactive isotopes. Those skilled in the art will see a great advantage to a faster, safer type of polynucleotide assay.

EXAMPLE

The Microcavity as a Microelectrochemical Immunosensor

Chemicals and materials. All chemicals were reagent grade and used as received. Aqueous solutions were prepared using high purity deionized (DI) water from a Millipore Milli-Q filtration system; model RG (Bedford, Mass.). A gold coin (Canadian Maple Leaf, 99.99%) and a chromium-plated tungsten rod (R. D. Mathis, Long Beach, Calif.) served as sources for metal deposition to make Au macrochips and microcavity electrodes. Silicon wafers (125 mm diameter and 365–406 ?m thick) with crystal orientation of (100), were obtained from Wacker Siltronic Corp. (Portland, Oreg.) and was used as substrates for the macrochips and microcavity electrodes. Polyimide (PI-2721, HD MicroSystems, Du Pont) was used according to DuPont specifications.

Affinipure rat anti-mouse IgG (1.3 mg/mL in 0.01 M Sodium Phosphate, 0.25 M NaCl, pH 7.6, heavy (H) and light (L) chains only, H+L, without the Fc region), Chrompure mouse IgG whole molecules (11.2 mg/mL in 0.01 M Sodium Phosphate, 0.5 M NaCl, pH 8.0), and alkaline phosphatase conjugated Affinipure rat anti-mouse IgG (0.7 mg/mL in 0.01 M Tris-HCl, 0.25 M NaCl, pH 8.0, H+L, without Fc region) were obtained from Jackson Immunoresearch Laboratory (West Grove, Pa.). Tris-(hydroxymethyl) aminomethane (Tris), bovine serum albumin fraction V powder (BSA), 1-pentanesulfonic acid (sodium salt), EDC, lithium chloride anhydrous, Tween 20, sodium azide, and p-aminophenol hydrochloride were obtained from Sigma-Aldrich (St. Louis, Mo.).

Palladium 10% w/w on activated carbon, 4-nitrophenyl phosphate disodium salt hexahydrate, cellulose PE1 TLC plates, MUOL, MUA, mercaptohexane (MH), potassium chloride, potassium nitrate, calcium chloride, and 18-mercaptooctadecane (MOD) were obtained from Aldrich (Milwaukee, Wis.). Absolute ethanol (200 proof) was obtained from AAPER (Shelbyville, Ky.). Ar gas and liquid N2 (nitrogen refrigerated liquid UN 1977) were obtained from PG Walker (Springdale, Ariz.). The glove bags were obtained from Instruments for Research and Industry (Cheltenham, Pa.). All other chemicals were from Fisher Scientific (Fair Lawn, N.J.). PAPP was synthesized and purified as previously described.66 Product verification was determined by H1 NMR (JEOL 270 Mz). The only peaks in the spectrum in D20 have chemical shifts at ???6.75 (doublet, 2 H, C6H4) and ???7.0 (doublet, 2 H, C6H4). There was no evidence of either unreacted starting material nor of PAP by NMR. An electrospray ionization mass spectrum of the product was also obtained in positive ion mode using a Bruker Esquire LC multipole ion trap mass spectrometer. It shows peaks at m/z 154, 234, 256 and 288 corresponding to the dephosphorylated fragment (disodium p-aminophenolate), protonated disodium PAPP, trisodium and monosodium dipotassium PAPP, at a peak ratio of 0.19:1:0.65:0.07, respectively.

Buffer solutions. The buffer solutions used in this study are as follows: a) PB: 0.1 M KH2PO4 and 6.2 mM Na2HPO4 in 14.3 mM NaCl at pH 6.0; b) acetate: 0.1 M sodium acetate and 0.1 M acetic acid at pH 5.5; c) acetate TBSA: 0.1 M sodium acetate-acetic acid, 0.05% (v/v) Tween 20, 0.2% (w/v) BSA, and 0.5 mM 1-pentanesulfonic acid at pH 5.5; d) 0.1 M Tris: 0.10 M Tris-(hydroxymethyl) aminomethane, 1 mM magnesium chloride, and 0.02% (w/v) sodium azide, pH 9.0 (adjusted with 6 M HCl or 6 M NaOH). Caution: Wear gloves when using NaN3 because it is a carcinogenic agent.

Fabrication of macrochips. Au macrochips (approximately 1.4 cm×2 cm, where the electroactive area is about 0.6 to 1 cm$_2$) were made from a 125 mm diameter silicon wafer substrate that bad 1.4 to 1.8 m SiO2 deposited on both sides at 250° C. by plasma enhanced chemical vapor deposition (PEVCD, Plasma Therm System VII). Deposition of a 15 μm adhesion layer of Cr and 1000 μm of Au was carried out using an Edwards Auto 306 TURBO thermal evaporator (Edwards High Vacuum Instrument International, West Sussex, UK). The Au macrochips were diced to size by hand using a diamond scribe. Polyimide (PI) macrochips were made using the Au macrochips as the starting substrate and spin coating a 4 μm thick layer of polyimide followed by cross-linking with UV light at 350 nm for 12 s and curing at 150° C. for 30 min and at 250° C. for another 30 min. The Au coated silicon wafer was spin-rinsed-dried (SRD) using ST 270D (Semitool, Calif.) for a total of 400 s before spin coating the PI. This process completely covers the Au so that the metal does not influence subsequent surface-modification experiments.

Figure 11:
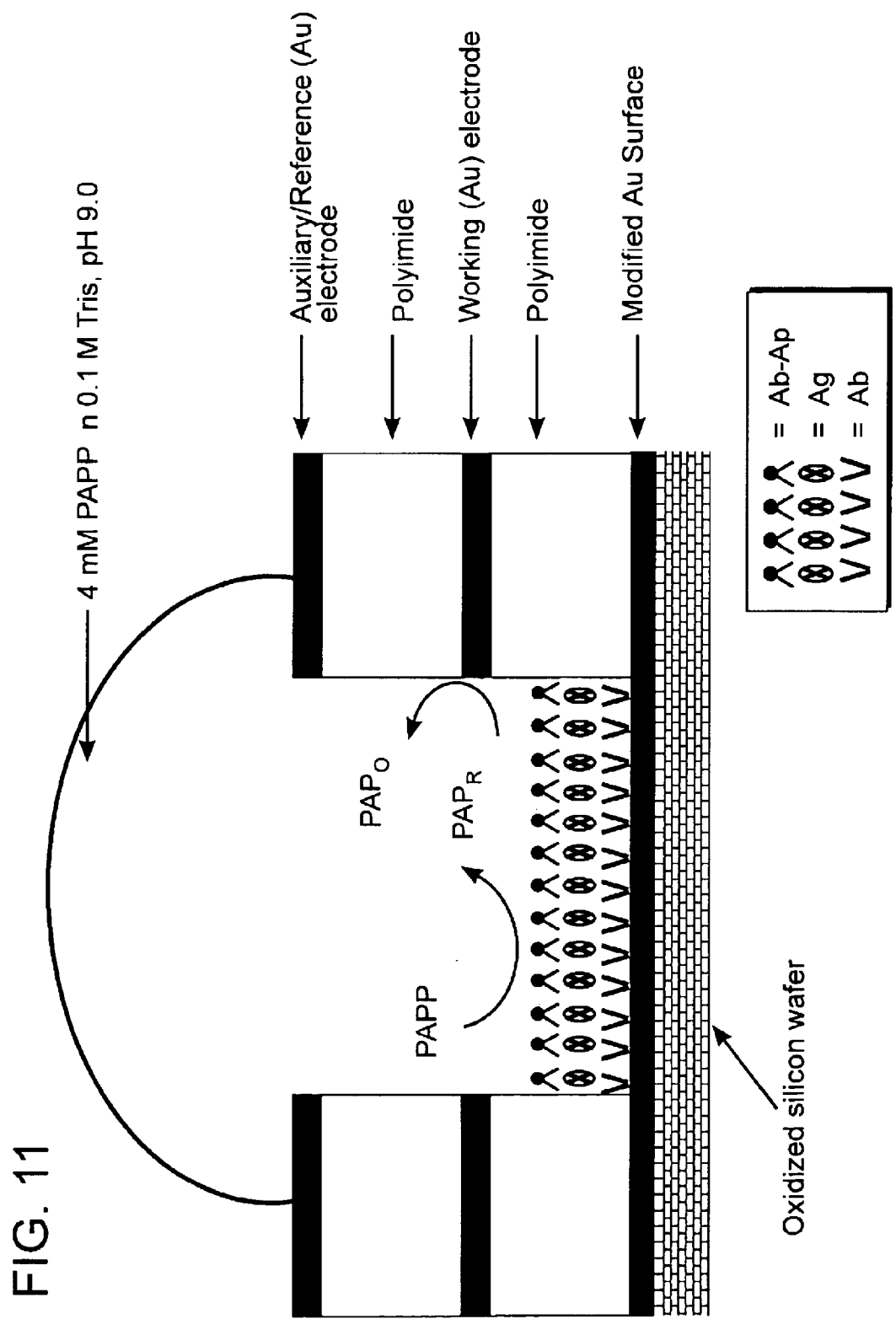
FIG. 11. Cross section schematic of a microcavity and diagram of how a microcavity may be converted into a self-contained, microelectrochemical immunosensor (not drawn to scale). Each metal layer is individually addressable, forming an RMD electrode at the bottom, a TNB electrode along the wall, and a top layer electrode around the rim. The conducting layers are composed of Au with a Cr adhesion layer and the insulating layers consist of 4-$\mu$m thick polyimide (PI). The sum of the two PI thicknesses essentially defines the depth of the microcavity. Rat anti-mouse IgG (Ab) forms the basis of the microelectrochemical immunosensor, and is immobilized on the RMD. This Ab captures the analyte, mouse IgG (Ag). A secondary antibody (rat anti-mouse IgG) that is conjugated to an enzyme, alkaline phosphatase, AP-Ab, is allowed to assemble onto the captured Ag. Afterwards, a drop of 4 mM p-aminophenylphosphate (PAPP) in 0.1 M Tris (pH 9) is placed on top of the microcavity to serve as the substrate for the enzyme label. The TNB is used as the working electrode, which can detect the p-aminophenol (PAPR) generated by the enzyme and the top layer Au serves as the reference/auxiliary electrode.

Fabrication of microcavity devices. Devices containing functional 50-μm microcavities were fabricated as previously described, where three patterned layers of Au (with corresponding Cr adhesion layers) are separated from each other by layers of PI on SiO2-coated silicon wafers (FIG. 11). The microcavities are formed by reactive ion etching through these layers, which exposes a RMD electrode at the bottom (50 μm in diameter and 8 μm deep), a TNB electrode along the wall of the microcavity (~500 Å wide and 157 μm long) and a top layer of gold at the rim. The microcavities were cleaned by sonicating (L&R PC3 Compact High Performance Ultrasonic Cleaning System) in acetone or water followed by rinsing with DI water. The chips were then dried with N2 gas and stored in DI water until needed. In an electrochemical study, electrode fouling in the microcavity can be eliminated by sonicating for 30 s in acetone or DI water and minimized by keeping the microcavity in a vial of DI water when not in use.

Macrochip studies to passivate the polyimide insulator. The extent of physisorption of active immunoassay components on PI was studied on PI-coated Au macrochips. Studies to eliminate physisorption involved pre-testing PI macrochips with different chemical species. The PI macrochips were then carried through all of the same steps of the immunoassay assembly both with or without SAMs of MUA or MUOL as those used to modify the Au macrochips (see assembly steps below). The activity of the modified PI surfaces to convert PAPP to PAPR was evaluated by electrochemical detection of the PAPR in the solution surrounding the PI surface. Pretreatment of PI macrochips involved exposing the chips to the one of the following solutions overnight: acetate TBSA, acetate TBSA then rinsed three times in DI water followed by exposure to 1.2 mM EDC for 10 min and exposure to 4 mM butanol overnight, acetate TBSA then rinsed three times in DI water followed by exposure to 1.2 mM EDC for 10 min and exposure to 4 mM propionic acid overnight, acetate TBSA then rinsed three times in DI water followed by exposure to 1.2 mM EDC for 10 min and exposure to 4 mM butanol with 4 mM propionic acid overnight, 4 mM 1-mercaptohexane, 4 mM diphenylamine (DPA), 4 mM MOD, 4 mM MOD in acetate TBSA, and 4 mM DPA in acetate TBSA. The 4 mM butanol, 4 mM DPA, 4 mM mercaptohexane, and 4 mM MOD were prepared in ethanol that was purged with Ar. The 4 mM propionic acid solution was prepared with DI water. The PI macro chips were separately soaked overnight in each of the different solutions. The macro chips dipped in solutions prepared in ethanol solvents were first rinsed three times with ethanol. Afterwards, all the chips were rinsed three times in DI water before exposure to subsequent solutions.

Microcavity pretreatment to passivate PI surfaces and electrode cleaning. The best approach for passivating immunoactivity on PI involved pretreatment with 4 mM MOD in acetate TBSA in an Ar-filled glovebag before assembling the immunoassay components. This pretreatment also passivates the gold surfaces of the microcavity device. Passivation was performed by exposing bare microcavity devices to 5 mL acetate TBSA with 4 mM MOD overnight. These were rinsed three times with acetate TBSA and dried with Ar. The passivating films on the RMD (before immunoassay components were assembled) and on the TNB and top layer gold (after immunoassay components were assembled) were removed by electrochemically cycling between +1.5 V to −0.5 V in electrolyte solution of 1 mM CaCl2 in 0.1 M KCl for at least 30 min at 30 V/s.67–69 An alternative procedure involved holding the potential at +0.7 V or −0.5 V in 1 mM CaCl2 in 0.1 M KCl solution for at least 30 min. Extent of electrode cleanliness and passivation was determined by CV in a solution of 4 mM K3Fe(CN)6, 1 mM CaCl2, and 0.1 M KCl.

After electrochemical desorption, the microcavities were cleaned by rinsing with DI water. The chips were dried with N2 gas and stored in DI water until needed. The modified chips are refrigerated in acetate TBSA.

Determination of immunoassay activity on the silicon wafer. To determine whether physisorption to silicon occurs during the macrochip immunoassays, silicon wafer pieces (approximately 1.4 cm×2 cm, without Au or PI) were subjected to the same surface modification processes used for the Au macrochips. The activity of the modified silicon wafer macrochips to convert PAPP to PAPR was evaluated by electrochemical detection.

Self-assembled monolayers. The Au macrochips were cleaned in piranha solution (30:70 (v/v) of 30% H2O2 and concentrated H2SO4) for 30 min and thoroughly rinsed for 30 min with running DI water before use. (Caution: piranha solution is strongly oxidizing, and should be handled with care!) SAM preparation, rinsing, and drying were carried out completely in an Ar-purged glovebag after the cleaning step to eliminate oxidation of SAMs by air (or ozone). The Au macrochips were soaked in solutions of either 4 mM MUA or 4 mM MUOL in Ar-purged ethanol for 24 h to form SAMs, followed by rinsing with Ar-purged ethanol three times in each of three separate test tubes inside the glovebag. The chips were dried with Ar and kept in closed vials before use. The same procedure was followed for the formation of SAMs on surfaces of the microcavity, with the exception that the microcavity devices were cleaned by sonication in ethanol for 30 s, instead of piranha solution.

Immobilization of the primary antibody. A working solution of 24 g/mL Ab and 1.2 ?M EDC in PB was prepared by combining appropriate volumes of stock solutions of 1.3 mg/mL Ab and 2.4 M EDC in PB, followed by dilution with PB buffer. All of the following steps for antibody immobilization were performed inside a glove bag filled with Ar. SAM-modified macrochips and microcavity devices (which were pre-tested with acetate TBSA and MOD, and for which passivation had been electrochemically removed from the RMD) were soaked in the Ab/EDC working solution for 2 h (1 mL for the macrochip and 200 ?L for the microcavity inside a water-saturated, parafilm-sealed petri plate). The EDC assists covalent attachment of the Ab to the free end of the SAMs.43, 59, 60 The chips were rinsed with 1 M NaCl three times and then soaked three times in acetate TBSA (1 mL for the macrochip for 15 min and 50 L for the microcavity for 30 s, each time) to eliminate non-specifically adsorbed Ab.

Capture of antigen, mouse IgG. Working solutions of the Ag were prepared by dilution of an 11.2 mg/ml Ag stock solution in 0.01 M sodium phosphate buffer in 0.5 M NaCl (pH 8.0) with acetate TBSA. Ab-immobilized macrochips were exposed to a 1 mL solution of 100 ng/mL Ag for 1 h and then rinsed three times with 1 mL of acetate TBSA for 15 min. The Ab-immobilized microcavities were exposed to varying concentrations of Ag ranging from 5 ng/mL to 100 ng/mL by leaving a 1 L drop of the solution on top of the microcavity for 10 min in a water vapor-saturated petri dish sealed with parafilm (to minimize evaporation). A 1 $\mu$L drop in this humid environment does not show any significant evaporation after 66 h at room temperature in the laboratory. The microcavity was rinsed with 50 L of acetate TBSA three times at 10 s each. These steps were performed outside of the glovebag.

Completing the immunoassay assembly with AP-Ab. A working solution of 700 ng/mL AP-Ab was prepared by diluting a 0.7 mg/mL AP-Ab stock solution in 0.01 M Tris-HCl in 0.25 M NaCl (pH 8.0) with acetate TBSA. Ab-immobilized macrochips that had been exposed to Ag and rinsed, were subsequently exposed to 1 mL of the AP-Ab working solution for 3 h and then rinsed by soaking three times in 5 mL of acetate TBSA for 15 min each to eliminate non-specifically adsorbed AP-Ab. Ab-immobilized microcavity devices that had been exposed to Ag and rinsed, were exposed to 1 L of the AP-Ab working solution for 10 min while inside a parafilm sealed water vapor-saturated petri dish and then rinsed three times with 50 L acetate TBSA for 10 s each. These steps were performed outside of the glovebag.

After deposition of the SAMs with the complete assembly (Ab+Ag+AP-Ab) on the microcavity devices, the passivation layers of the top layer Au and TNB were removed using the same procedures that were used for the removal of the passivation at the RMD. The cleaned TNB and the top layer Au could then be used as working and combination pseudoreference/auxiliary electrodes, respectively.

Enzymatic generation of PAPR. The enzyme substrate solution was 4 mM PAPP in 0.1 M Tris at pH 9.0, as previously described. The solution was purged with Ar and kept from light to minimize oxidation. Macrochips, containing the complete immunoassay assembly, were rinsed three times with 5 mL 0.1 M Tris at pH 9.0 at 10 min each before soaking in 5 mL of Ar-purged (15–30 minutes) PAPP solution inside a sealed beaker wrapped in aluminum foil for 24 h inside a glove bag filled with Ar. Microcavity devices, containing the complete assembly and electrochemically-cleaned TNB and top layer electrodes, were rinsed three times with 10 L Tris for 10 s and dried with Ar. The drop size of PAPP solution placed over the microcavity (inside an Ar-filled glovebag) was 200 nL, and the time for enzymatic conversion varied from 30 s to 2 min. The exact volumes and times for specific experiments are described in the text.

Surface characterization. The various stages of surface modification on Au macrochips were studied using polarization-modulation Fourier transform infrared reflectance absorption spectroscopy (PM-FTIR) with a Mattson Instruments Research Series 1 instrument. The IR beam was focused onto the sample at an incident angle of 77°. The beam was p-polarized and passed through a ZnSe Series II photoelastic modulator (Hinds) operating at 37 kHz before reaching the cooled HgCdTe detector. Spectra were taken with 4 cm$^{-1}$ resolution and a half-wavenumber of 2900 cm−1. PM-FTIR spectra were normalized by fitting the differential reflectance spectrum between 4000 cm−1 and 2100 cm$^{-1}$ and between 2500 cm$^{-1}$ and 800 cm−1 to 3rd order polynomial backgrounds using FitIT curve fitting software (Mattson). After curve fitting, the spectra were truncated and converted to absorbance using a WinFirst macro, written in-house under the specifications of Mattson. The sample chamber was purged with dry CO2-free air from Balston air dryer (Balston, Inc., Haverhill, Mass.). Each modified chip was kept in a vial filled with Ar prior to PM-FTIR analysis.

Electrochemical measurements. A BAS-100B potentiostat and a PA-1 preamplifier with BAS-100W electrochemical software (Bioanalytical Systems, Lafayette, Ind.) were used to perform CV. A Low Current Module and Faraday cage were used for electrochemical experiments on all microcavity devices. All electrochemical experiments involving a small drop of solution on the microcavity involved placing both the device and drop in a petri plate containing water droplets and cotton tips soaked in water to minimize evaporation. Two additional open petri plates containing water were placed inside the Faraday cage to keep the air humid. Initial electrochemical characterization of all electrodes was performed in a solution containing 4 mM K3Fe(CN)6, 1 mM CaCl2, and 0.1 M KCl. When the Au macrochips and top layer Au of the microcavity devices were characterized, a Pt flag auxiliary electrode and Ag/AgCl (saturated KCl) reference electrode were used. When the RMD and TNB electrodes of the microcavity devices were characterized, an internal setup was used, where the top layer Au served as a combination auxiliary/pseudoreference electrode.

Immunoassay activity of modified Au and PI macrochips was determined by evaluating the surrounding PAPP solution electrochemically for the presence of PAPR using an external setup of a bare Au macrochip working electrode, a Pt flag auxiliary electrode, and a Ag/AgCl (saturated KCl) reference electrode. Working electrode potentials were kept within appropriate ranges to avoid electrochemical conversion of PAPP into PAPR. The Au underlying the modifying layer was never used to detect the enzymatically-generated PAPR.

In the small volume, self-contained, electrochemical immunoassay studies using the microcavity device, immunoassay activity at the modified RMD was determined by evaluating the 200 nL drop of PAPP solution electrochemically for the presence of PAPR using an internal setup, where the TNB served as the working electrode and the top layer functioned as a combination auxiliary/pseudoreference electrode. The RMD underlying the modifying layer was never used to detect the enzymatically-generated PAPR.

Modification and characterization of gold macrosubstrates. Studies using SAMs of MUA and MUOL83–86 for immobilization of protein 83–85 and DNA86 have been previously reported. However, to our knowledge, this is the first report of using MUA and MUOL SAMs for immobilization of rat-anti mouse IgG to gold surfaces in a sandwich-type ELISA for detection of mouse IgG. Consequently, we performed several characterization and activity studies of the modified surfaces. Previously reported studies have used thioctic acid and cysteamine for immobilization of anti human IgE on piezoelectric quartz crystal with gold electrodes. Thioctic acid SAMs have been used for the detection of mouse IgGI and rabbit IgG.16 Butanethiol SAMs have been used for rabbit IgG detection.16 Photoimmobilization of mouse IgG on Au has been accomplished using SAMs of 10,10'-dithiobis(decanoic acid N-hydroxysuccinimide ester) terminated alkyl disulfide.80 Previous studies have used various SAMs to attach proteins other than IgG.

Figure 12:
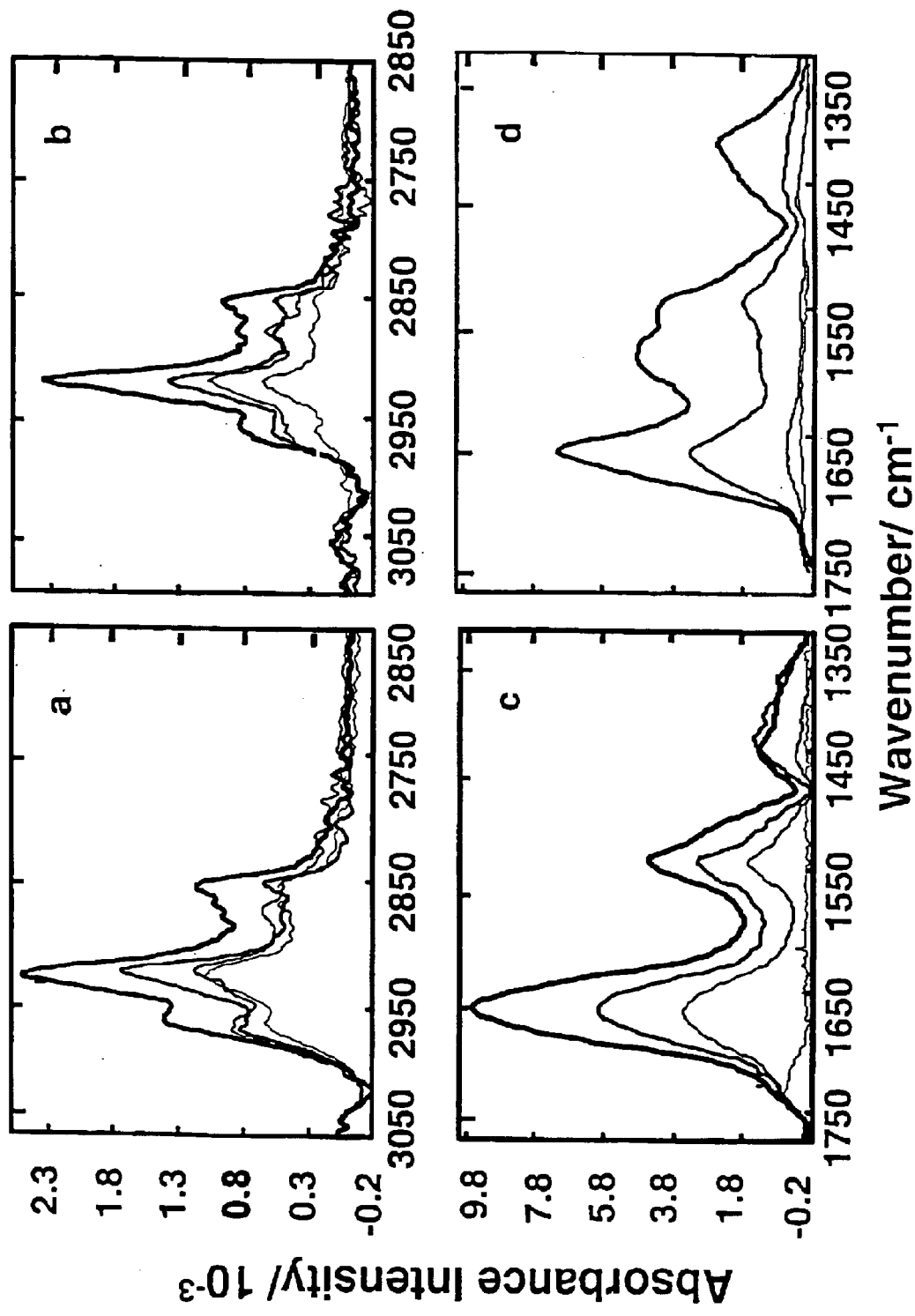
FIG. 12. PM-FTIR spectra of modified surfaces on Au macrochips. a) C—H stretching region with MUA SAMs b) C—H stretching region with MUOL SAMs c) Amide region with MUA SAMs d) Amide region with MUOL SAMs. Absorbance increases after each subsequent step in the immunoassay assembly: SAM, Ab, Ag, and AP-Ab.

Representative PM-FTIR spectra of Au macrochips at the various stages of surface modification are shown in FIG. 12. As expected, each stage of modification (SAM, Ab, Ag, and AP-Ab) exhibited a corresponding increase in absorption in the vibrational modes of both the C—H stretching ( ) region90–93(CH3 as 2960 cm-1, CH3 sy 2870 cm-1, CH2 as 2920 cm-1, CH2 sy 2855 cm-1)41 and the amide region (C═O amide I at 1675 cm-1, N—H amide II at 1545 cm-1, and C—N amide III at 1445 cm-1 92, 94, 95 where ìasî is asymmetric and ̀ssŷi is symmetric.

Figure 13:
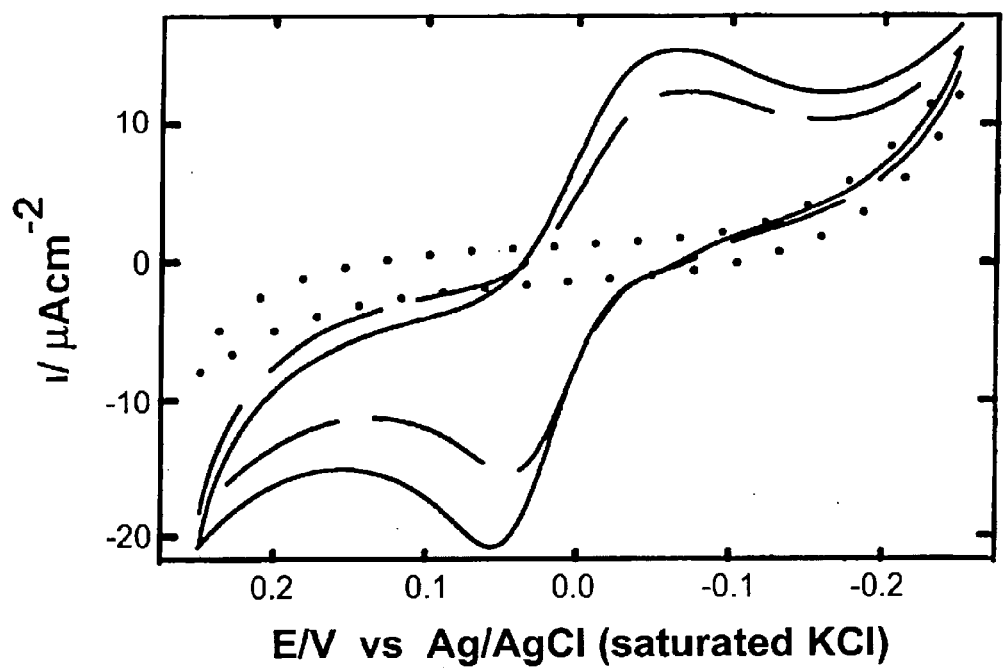
FIG. 13. Demonstration of the necessity of SAMs in the activity of the immunoassay components. CV responses at 25 mV/s using an external setup in 5 ml of 4 mM PAPP in 0.1 M Tris buffer, after the modified Au macrochip had been soaked in the solution for 24 h. Only Au macrochips containing the complete assembly (Ab+Ag+AP-Ab) with SAMs resulted in a signal that indicated formation of PAPR; MUOL+complete assembly (solid curve), MUA+complete assembly (dashed curve), and complete assembly without SAMs (dotted curve).

Immunoactivity of modified surfaces and the role of self-assembled monolayers was investigated by detecting the enzymatically-generated PAPR at a nearby bare electrode. The solid and dashed curves in FIG. 13 show typical CV responses using an external electrode setup in a solution of 4 mM PAPP and 0.1 M Tris, in which a modified Au macrochip surface (SAM+complete assembly) had been soaked for 24 h. Higher currents were obtained when the SAM component of the modified surface was prepared with MUOL than with MUA.

When immunoactivity was investigated at bare Au macrochips that had been exposed to all of the steps in the complete assembly but without the SAM component, no PAPR was detected. The CV response is shown in FIG. 13 (dotted curve). Nevertheless, PM-FTIR shows significant amounts of physisorption of the individual components of the immunoassay to the Au macrochip in the absence of the SAMs (data not shown). These results suggest that the SAMs are necessary to maintain the active conformations of the immunoassay components on the gold. In addition, physisorption, if any, to the silicon dioxide on the back side of the chip must not contribute to the generation of PAPR. In fact, silicon wafer macrochips that were subjected to the same surface modification steps as Au-coated macrochips showed no electrochemical activity. The specific activity at SAM sites is a useful phenomenon, because it can be used to facilitate the construction of arrays of multi-analyte microimmunoassays.

Elimination of physisorption of active species on polyimide. Before transferring the surface modification procedure established for the Au macrochip to the RMD of the microcavity, the adsorption of immunoassay components to polyimide was studied. Polyimide forms the 4 $\mu$m thick insulator between metal layers and essentially serves as the main material along the walls of each microcavity. Because the desired immunoassay configuration involves a selectively-modified RMD using electrochemistry to control the site of modification, it would be counterproductive if immunoassay components were to physisorb uncontrollably in their active forms to the surrounding walls.

Figure 14:
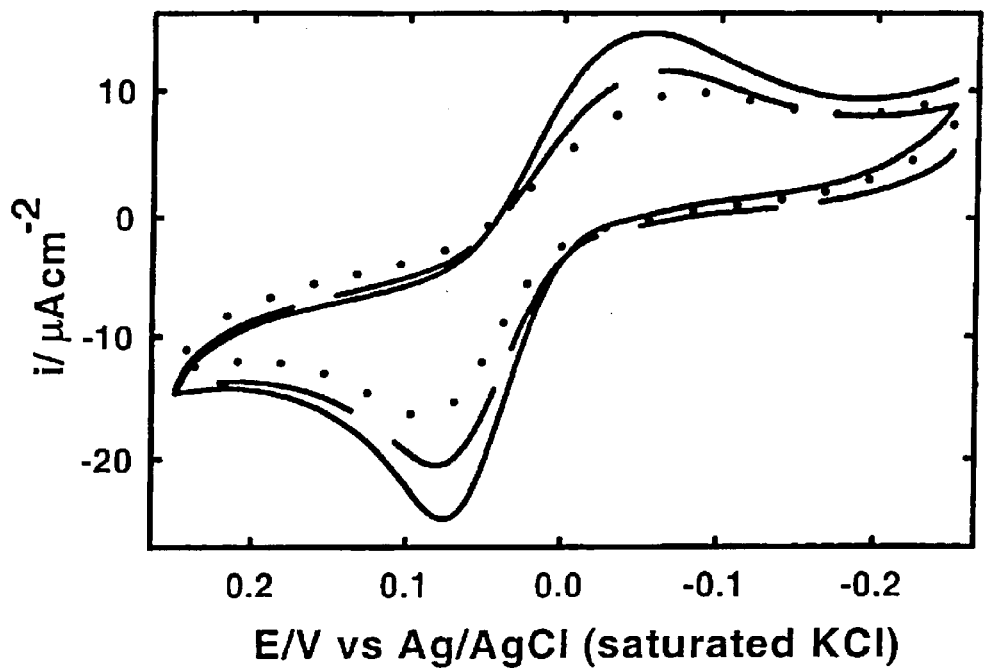
FIG. 14. Determination of physisorbed, active immunoassay components on PI. CV responses were obtained at 25 mV/s using an external setup in 5 ml of 4 mM PAPP in 0.1 M Tris buffer, after the modified PI macrochip had been soaked in the solution overnight inside an Ar-filled glovebag. PI macrochips were treated under the following conditions prior to soaking in the PAPP solution: MUOL+complete assembly (dashed curve), MUA+complete assembly (dotted curve), and complete assembly without MUOL or MUA (solid black curve).

Polyimide-coated Au macrochips were subjected to the same surface modification processes as the Au macrochips. Note that no Au is exposed on the PI coated chips so that chemistry is confined to the PI on one side of the substrate and silicon dioxide on the other side. The macrochips were then placed in a PAPP solution for 24 h and CV was obtained at a gold electrode in an external setup arrangement to detect PAPR. The electrochemical responses in FIG. 14 show that the complete assembly with and without the MUOL or MUA exhibited significant generation of PAPR, thereby, indicating that the immunoassay components physisorbed in an active form on the polyimide.

Figure 15:
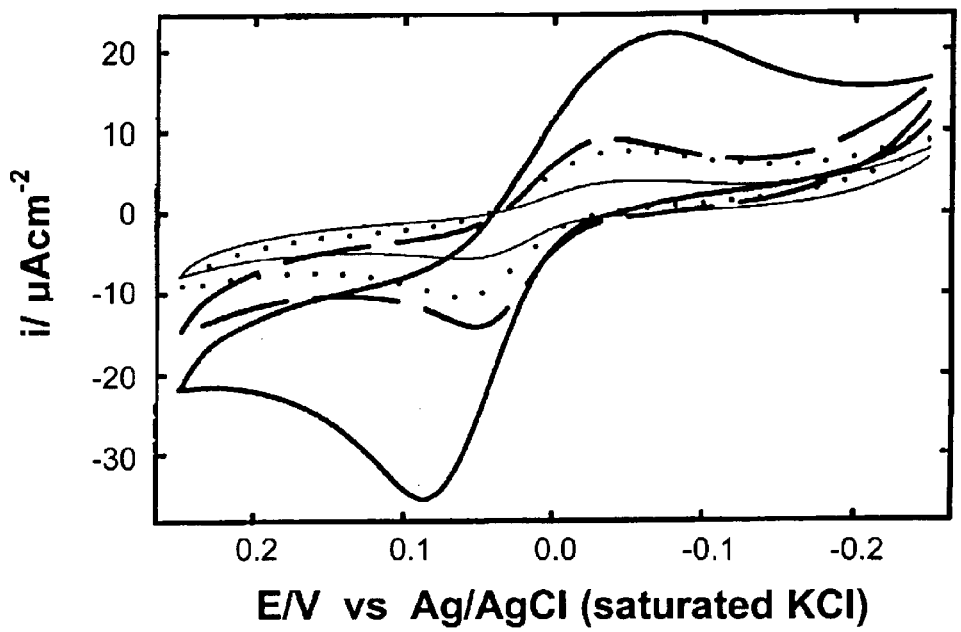
FIG. 15. Evaluation of different PI-pre-treatment for elimination of immunoactivity. Complete assembly using MUOL was performed after the pretreatment. Electrochemical detection of PAPR is similar to that described in FIG. 14. Decreasing CV responses were obtained from the following PI pre-treatment: no pretreatment (thick solid curve), acetate TBSA+4 mM propionic acid (dashed curve), acetate TBSA+4 mM butanol (dotted curve), acetate TBSA+4 mM butanol+4 mM propionic acid (thin solid curve).

Several strategies were investigated to eliminate the activity on the PI. One approach involved first exposing the PI to acetate TBSA solution in order to block possible protein adsorption sites before proceeding with the immunoassay assembly. The results in FIG. 15 show a decrease in the PAPR current. Assuming the residual activity to be caused by covalent attachment of the Ab to —NH2, —OH, and —COOH functional groups of amino acids of BSA, steps were taken to protect these sites covalently by subsequently exposing substrates to EDC and butanol and propionic acid. This resulted in further decrease but not total elimination of the PAPR signal. Thus, it seems that PI may have multiple sites of physisorption, which have different affinities for different proteins, or that the size of BSA might prevent complete coverage of those sites.

Figure 16:
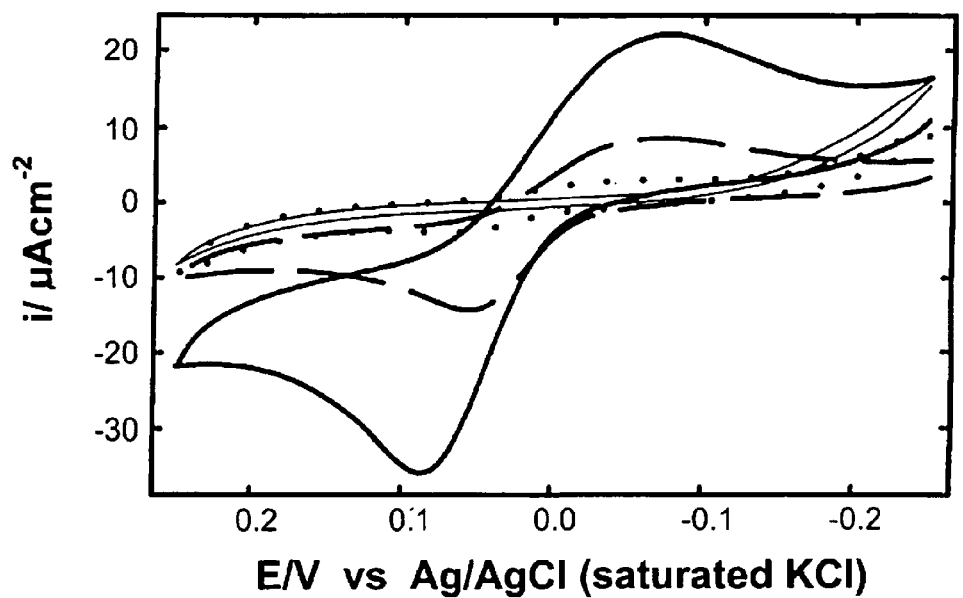
FIG. 16. Continued evaluation of pre-treatment to passivate PI. Same as description in FIG. 6. Decreasing CV responses were obtained from the following PI pre-treatment: no pretreatment (thick solid curve), acetate TBSA (dashed black curve), acetate TB SA+DPA (dotted curve), acetate TBSA+MOD (thin solid curve). Complete elimination of the current signal is achieved with the latter pretreatment.

The second approach to passivate PI activity toward the immunoassay components involved attempts to form more hydrophobic sites on the PI, which should change the nature of the protein adsorption. Thus, the PI was exposed to small molecules of a more hydrophobic nature (MH, MOD, and DPA). Solutions that were tried are described in the Experimental Section. Pretreatment of the PI macrochips with DPA, MH, MOD, and a mixture of MH and MOD in ethanol showed a 50% decrease in signal but did not completely eliminate the activity of the immunoassay (data not shown). FIG. 16 compares results for the two best PI pre-treatment to those for acetate TBSA pretreatment and for no pretreatment. A combination of acetate TBSA with 4 mM MOD completely passivated the PI. At present we do not know why this process provides successful elimination of the immunoactivity and the others do not. The acetate TBSA+MOD pretreatment was chosen for use with microcavity devices to prevent physisorption of active immunocomponents on the PI.

Electrochemical removal of passivating layers at gold surfaces. Not only does soaking the microcavity devices in acetate TBSA with 4 mM MOD passivate the PI, but it also passivates the RMD, TNB, and top layer Au, as demonstrated in FIG. 17. This is an advantage, because it essentially protects the electrode surfaces from fouling during the immunoassay assembly process. Electrochemical desorption, was performed to remove passivation specifically at the RMD. CV in Fe(CN)63-solution, FIG. 17, demonstrates that passivation at the RMD is removed but not at the TNB and the top layer gold. The clean RMD was then subjected to the procedure for assembling the SAMs and the immunocomponents (Ab+Ag+AP-Ab).

Figure 17:
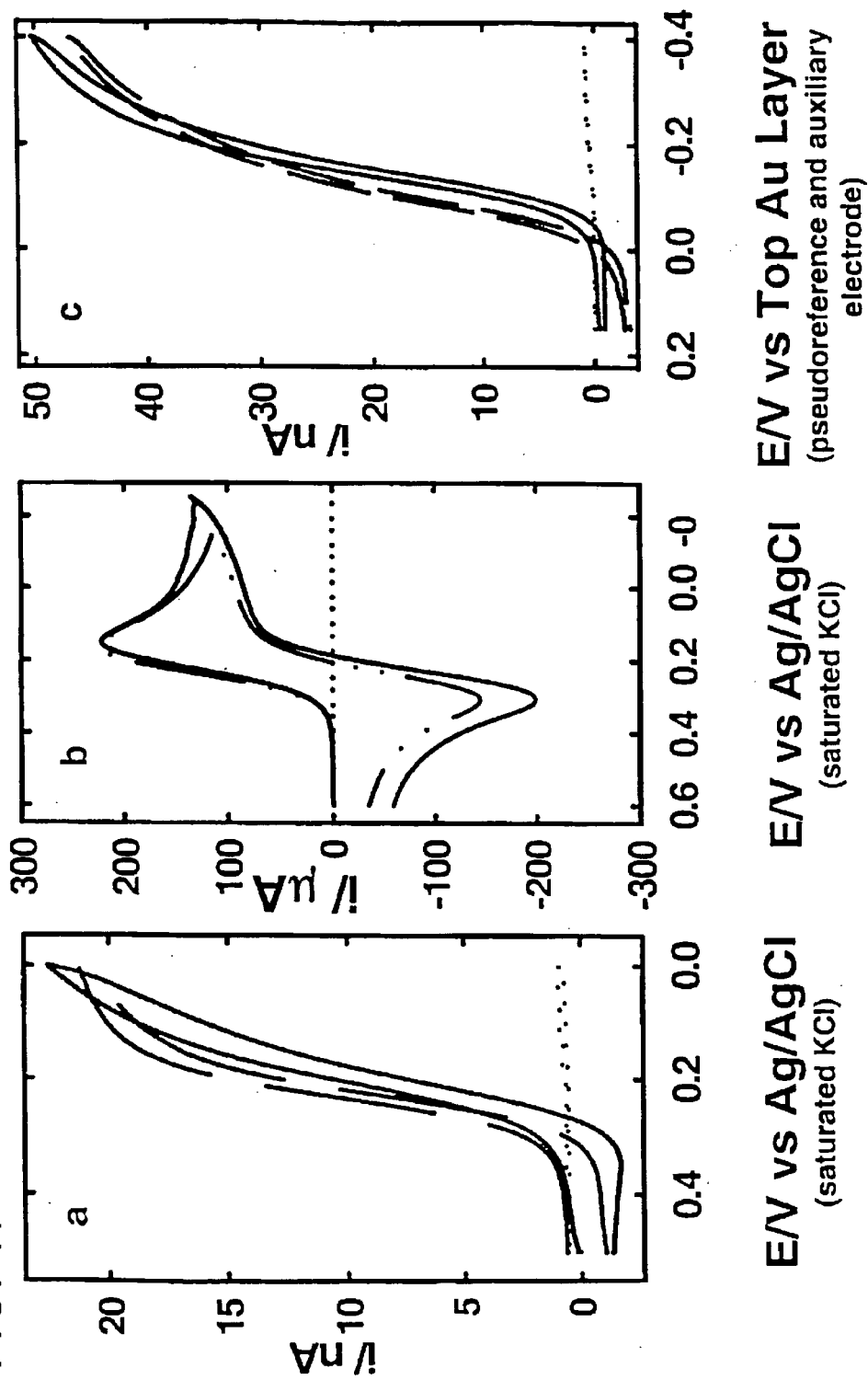
FIG. 17. Effect of passivation with acetate TBSA+4 mM MOD and subsequent electrochemical cleaning of different microcavity electrodes. CV responses at what scan rate 50 mVs-l were obtained in a solution of 4 mM K3Fe(CN)6, 1 ?M CaCl2, and 0.1 M KCl electrolyte, before passivation (solid curve), after passivation (dotted curve), and after electrochemical cleaning (dashed curve). The following served as working electrodes: a) RMD using external setup. b) Top Layer Au using external setup, and c) TNB using internal setup with TNB as working electrode and the top layer Au as pseudo reference and auxiliary electrodes. Electrochemical cleaning involved cycling the potential between +1.5 and ñ0.5 V and/or holding the potential at +0.7 V.

Only after deposition of the MUOL or MUA SAMs with the complete assembly at the RMD were the passivating layers on the top layer Au and the TNB removed using electrochemical desorption. The CV responses in Fe(CN)63-solution before and after electrochemical desorption at the TNB and top layer Au are shown in FIGS. 16 and 17. The cleaned TNB and the top layer Au could then serve as working and pseudoreference/auxiliary electrodes, respectively, to detect PAPR, enzymatically-generated at the modified RMD upon addition of PAPP solution to the microcavity (see FIG. 17).

Figure 18:
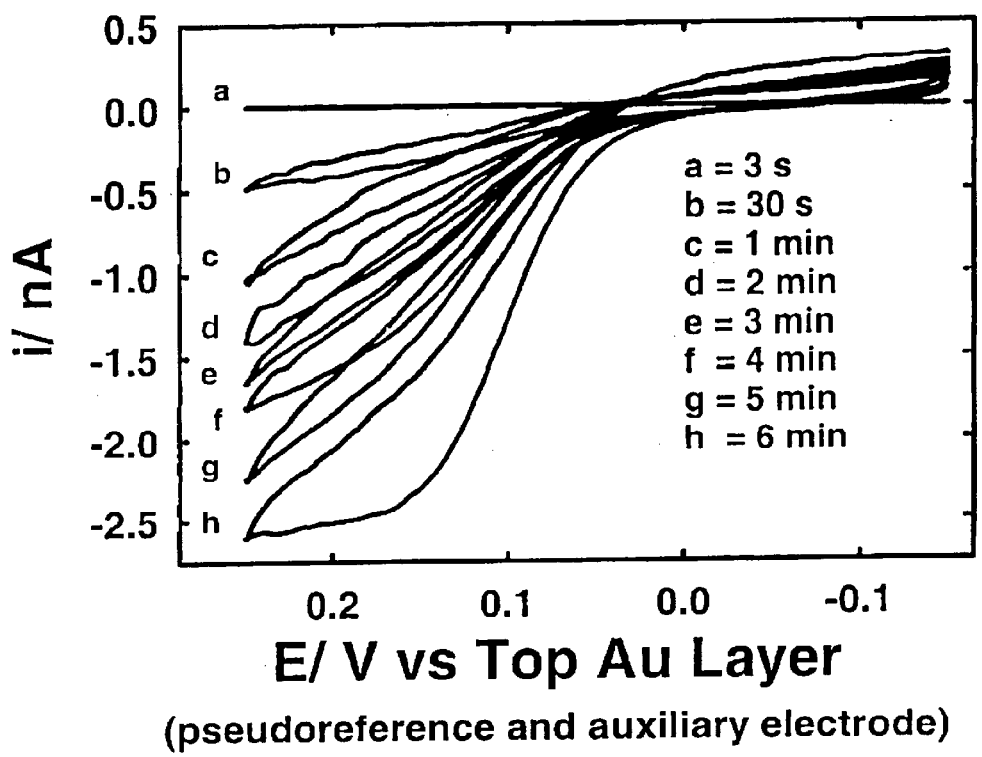
FIG. 18. Timed CV responses at 50 mV/s using a 200 nL drop of 4 mM PAPP in 0.1 M Tris buffer at a self-contained microelectrochemical immunosensor containing MUOL+ complete assembly with 100 ng/ml mouse IgG. About five seconds after the drop of 4 mM PAPP was placed on top of the microcavity, CV was performed, which provided the initial response. A second response was obtained after 30 s from the time the drop was placed on top of the modified cavity that indicated a significant increase from the initial response. Subsequent responses were taken at 30 s intervals up to 6 min. (For clarity, not all data are shown.)

Site-specific, self-contained, small volume microelectrochemical immunoassay in a microcavity. A proof-of-concept was demonstrated using a 50-$\mu$m diameter microcavity where steps had been taken to eliminate the physisorption at the PI, the surface of the RMD had been modified with MUOL+Ab+Ag+AP-Ab (see FIG. 17), and the top layer of Au and the TNB were electrochemically cleaned. The TNB served as the working electrode and the top layer Au served as the pseudoreference/auxiliary electrode. The volumes of solutions containing Ag and AP-Ab that were used during the assembly were 1 $\mu$L. For comparison, the smallest sample volume (which is not allowed to dry) for electrochemical ELISAs reported in the literature and commercially available for mouse IgG is 10 $\mu$L.1 Thus, our sample volume exhibits at least a 10 fold improvement. CV responses at increasing time increments to a 200 nL drop of the PAPP solution that was placed on top of the modified microcavity are shown in FIG. 18. The volumes of PAPP solution previously reported in the literature are 20 $\mu$L or larger. Hence, our system has accomplished enzyme substrate volume reduction by two orders of magnitude. Even smaller volumes with our system are possible (16 pL for the 50-$\mu$m diameter cavity and 0.6 pL for the 10-$\mu$m diameter cavity), because working and auxiliary/reference electrodes are located within the microcavity. But because of complications with small sample manipulations and evaporation issues, we only report volumes of 200 nL here. Future work will address the smaller volumes.

At only 30 s after the drop of PAPP solution was placed on top of the modified microcavity, a measurable current of the enzymatically-generated PAPR was recorded at a scan rate of 50 mV/s. This quick measurable response is presumably due to the short distance between the closely spaced working electrode and modified surface (resulting in steep concentration gradients) and to the geometry (PAPR can only escape from the microcavity by passing by the TNB, although collection efficiency is not 100%). This is a significant improvement over studies (excluding SECM), which require incubating the modified electrode in PAPP or PNPP for 5 to 30 min before performing electrochemical detection. Subsequent responses exhibit increasing plateau currents, as shown in FIG. 25, due to continuous enzymatic generation of PAPR. Because detection of PAPR in our system occurs almost immediately after placing the drop on the microcavity, the fraction of PAPR that is present from non-enzymatic hydrolysis, which could add an unknown background signal that increases exponentially at times beyond 20 min, 47 is minimal. The self-contained microelectrochemical immunoassay experiments also eliminate the need for transfer of solutions because enzymatic generation and detection are carried out in the same space. The total assay time, starting with the addition of Ag solution to the modified cavity and ending when PAPR is detected, (excluding the electrode-cleaning steps) is 24 min. For comparison, commercial ELISA for mouse IgG has a total assay time (over the same steps) of 1.5–3 h.96

Figure 19:
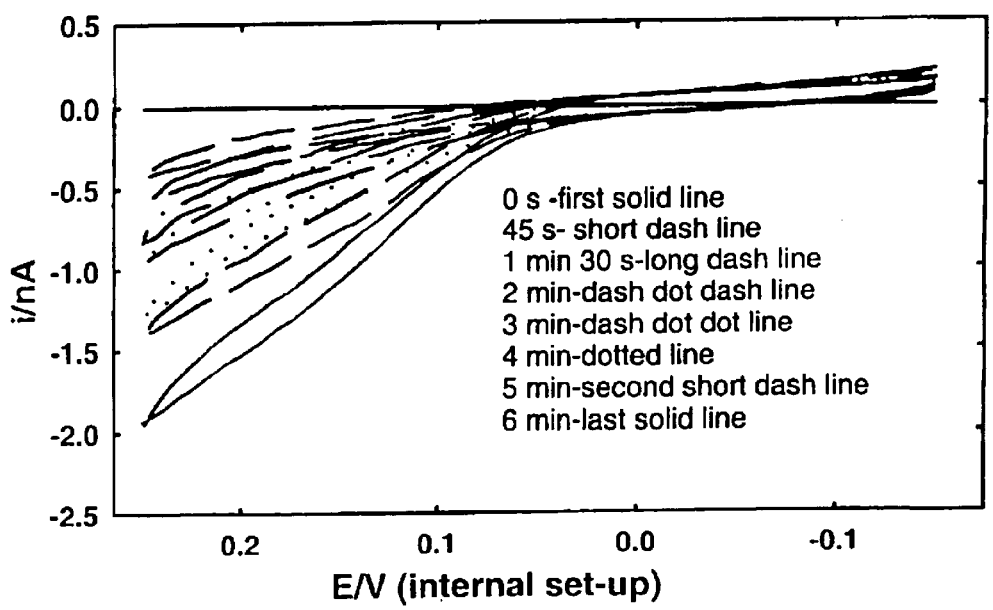
FIG. 19. Timed CV responses using a 0.5 L drop of 4 mM PAPP (in Tris buffer) from a self-contained microelectrochemical immunosensor containing MUOL+complete assembly with 100 ng/ml mouse IgG at 50 mV/s. About five seconds after the drop of 4 mM PAPP was placed on top of the microcavity, a current reading was recorded at a scan rate of 50 mV/s that served as the initial response. A second response was recorded after 45 s that indicated a significant increase from the initial response. Subsequent responses were taken at 30 s intervals up to 6 min.

Using a microcavity with surface modification containing MUOL+Ab+Ag+AP-Ab at the RMD, the TNB as working electrode and the top layer Au as the reference and counter electrodes, the timed CV response to 0.5 L (and 0.2 L, not shown) of 4 mM PAPP placed on top of the modified microcavity is illustrated in FIG. 19. The volume of PAPP reported in previous literature was 20 L or higher. Hence, our system has accomplished enzyme substrate volume reduction by two orders of magnitude.

About five seconds after the drop of 4 mM PAPP was placed on top of the microcavity, a current reading was recorded at a scan rate of 50 mV/s that served as the initial response. A second response was recorded after 45 s that indicated a significant increase from the initial response. Subsequent responses are shown in FIG. 19. Previous studies have reported incubating the modified electrode in PAPP or PNPP for 5 to 30 min before performing the potential scan. Our system allows performance of the potential scan right after the drop is placed on the microcavity. This eliminates the generation of PAPR from non-enzymatic hydrolysis that adds an unknown background signal that increases exponentially at times beyond 20 min.

The data in FIG. 19 indicates that the self-contained electrochemistry inside the microcavity has been harnessed to eliminate the need for an external reference and counter electrode in an electrochemical immunoassay. At the same time, the biological component of the immunoassay is contained at the bottom of the same cavity, thereby eliminating the need to transfer the solution as previously reported.

Figure 20:
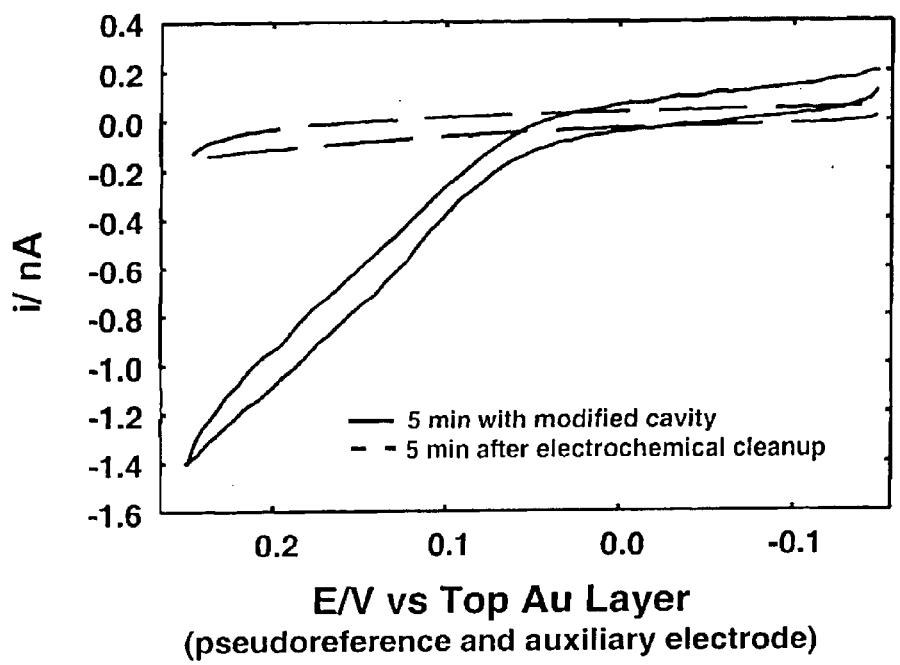
FIG. 20. Demonstration that immunoactivity occurs only at the modified disk in the microcavity and that polyimide-passivation is successful. CV responses are of a self-contained microelectrochemical immunosensor (50 ng/mL IgG) after 5 min in 500 nL 4 mM PAPP IN 0.1 M Tris, pH 9.0, before (solid line) and after (dashed line) electrochemical removal of the modifying layer (MUOL+Ab+Ag+AP+Ab) at the RMD (50 mV/s, TNB=working, top layer Au=auxiliary/reference).

To determine if modification at the RMD was the only site of immunoactivity in the microcavity, the RMD of an active microelectrochemical immunosensor was subjected to selective electrochemical cleaning to remove the adsorbed substances. The results before and after removal of immunoassay components at the RMD are shown in FIG. 20, and confirm that immunoactivity is absent from the polyimide walls, the TNB, and the top layer of gold. This demonstrates that the PI passivation chemistry is successful, and that subsequent surface chemistry can localize the immunoactivity of these devices.

Figure 21:
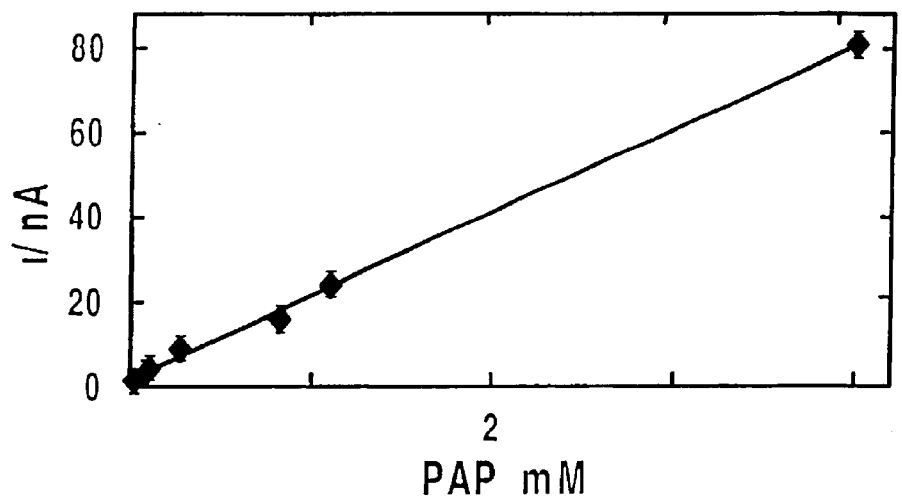
FIG. 21. The sensitivity of the microcavity toward detection of PAPR was evaluated by establishing a calibration curve. CV at 50 mV/s was carried out on PAPR solutions (200 nL each) of different concentrations ranging from 5.00 ?M to 3.98 mM that were placed top of the 50 m cavity. The calibration curve, which plots the plateau current for the average of two sets of experiments for each concentration of PAPR gave a linear curve with a PAPR detection limit of 4.4 nM or 880 fmol. (TNB=working, top layer Au=auxiliary/reference).

Sensitivity and detection limits of the microelectrochemical immunoassay. The performance of a microcavity for detection of PAPR was evaluated via a calibration curve. This was done by monitoring the CV responses after placing a 200 nL drop of PAPR solution of different concentrations ranging from 5.00 mM to 3.98 nM directly on a 50-$\mu$m diameter cavity. The current (average of two measurements) is linear with concentration and is shown in FIG. 21. A detection limit of 4.4 nM or 880 fmol (or 128 pg) was calculated using the typical equations at the 99%+ confidence level (t is ~3 and there are 16 degrees of freedom),97 where the slope from the calibration curve is 19.7 0.8 nA/mM, and the standard deviation from the blank signal (17 measurements) from a 200 nL drop of 0.1 M Tris is 29×10−6 nA.

The predicted slope for the calibration curve at the TNB in PAPR solutions is 8.5 nA/mM, based on the analytic expression for the theoretical diffusion-limited current at an in-plane band electrode at all times (when either radial, planar, or both forms of diffusion contribute) which is described by Szabo et al.98 The value of time used in this calculation is the time it takes to sweep from the E1/2 value to the potential at which the current was measured on the reducing side of E1/2. The diffusion coefficient of PAP used is 0.79×10−5 cm2s−1.99 The equation may be adapted to the tubular band geometry in an infinitely long tube as long as the diameter-to-electrode width ratio exceeds 100.100 The average current for a 4 mM solution from the two sets of experiments used to obtain the calibration curve for PAPR in FIG. 21 is 80.9 nA, which is much larger than the theoretical value, 34 nA. This may be due to a larger TNB electrode area than expected (some undercutting may occur during the etching process), and access to redox species in a larger volume of solution once the diffusion layer exceeds the confines of the microcavity, and redox equilibrium with bulk solution species through the top metal layer. Current did vary from device to device and from one fabrication batch to another. For example, on average across many devices (n=12), the CV plateau current for a 4 mM PAPR solution is 54 nA with a standard deviation of 18 nA.

Figure 22:
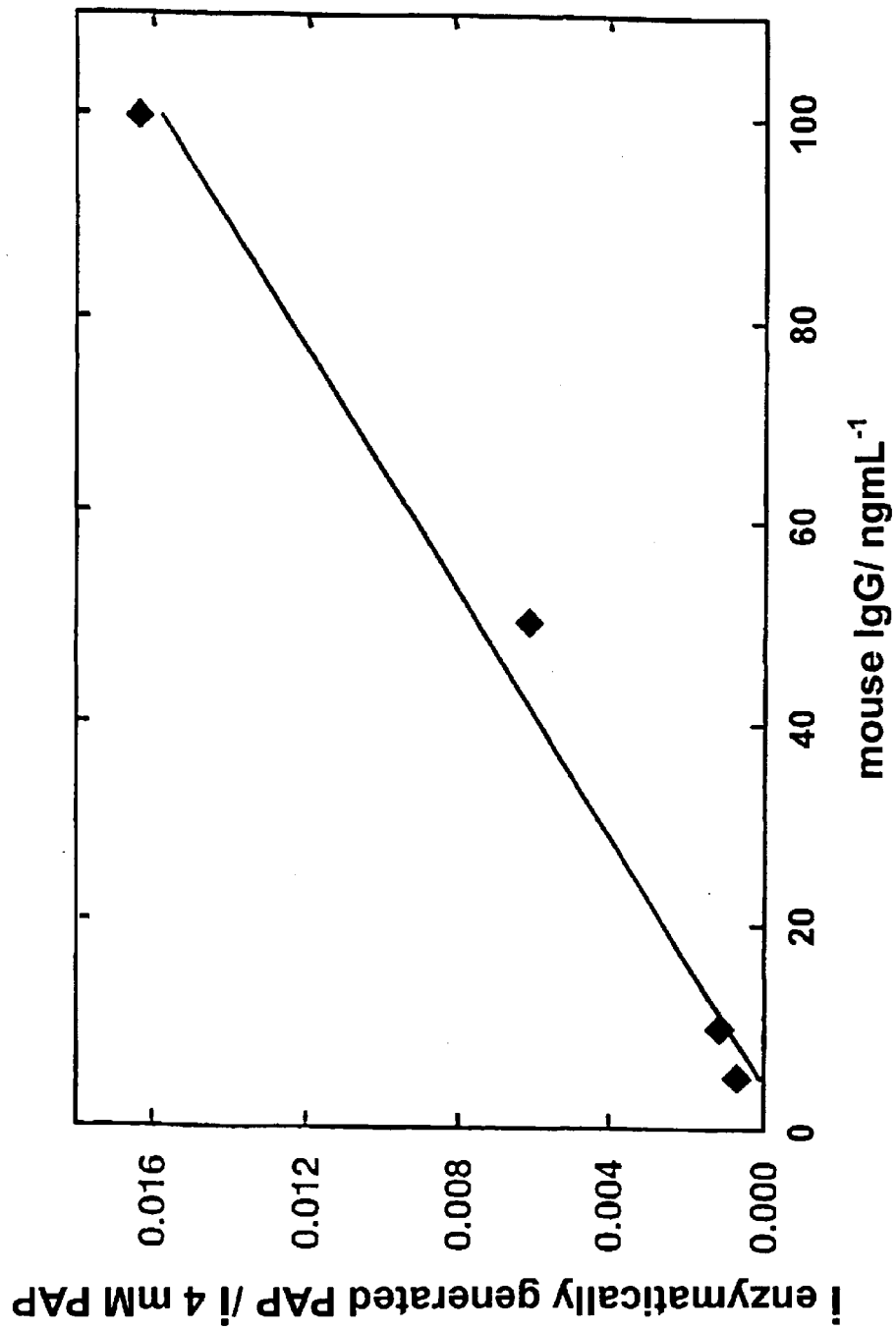
FIG. 22. Calibration curve for mouse IgG concentrations ranging from 5 to 100 ng/ml with a detection limit of 56 zmol. The current readings (after 2 min in 200 nL of 4 mM PAPP in 0.1 M Tris, pH 9.0) were divided by the current signal from 200 nL of 4 mM PAPR in 0.1 M Tris pH 9.0, (50 mV/s, TNB=working, top layer Au=auxiliary/reference) using each cavity prior to modification.

The low detection limit that was obtained in studies of PAPR solutions at a bare microcavity suggest that low detection limits of IgG at modified microcavities may be possible from the enzymatically-generated PAPR. A calibration curve for mouse IgG (FIG. 22) was obtained from CV responses (50 mV s−1) to PAPR generated after 2 min in a 200 nL drop of 4 mM PAPP in 0.1 M Tris (pH 9.0) at two different microelectrochemical immunosensors for each of four different concentrations of IgG (5, 10, 50, and 100 ng/ml). Each immunosensor was prepared using a 1 ?L drop of IgG solution. Because a different microcavity was involved for each concentration, it was necessary to normalize the immunosensor response. The enzymatically-generated response at each modified microcavity in 4 mM PAPP solution was divided by the response under similar conditions at the bare microcavity (before modification) in 4 mM PAPR. The resulting number represents the normalized signal, which should be less than or equal to one. A least squares line through the points in the calibration curve produces a slope of 0.165±0.007 mL/ng. The detection limit, using the slope from this line, was determined to be 56 fM (9 pg/mL) or 9 fg (56 zmol) of mouse IgG on a 1 $\mu$L drop.

Figure 23:
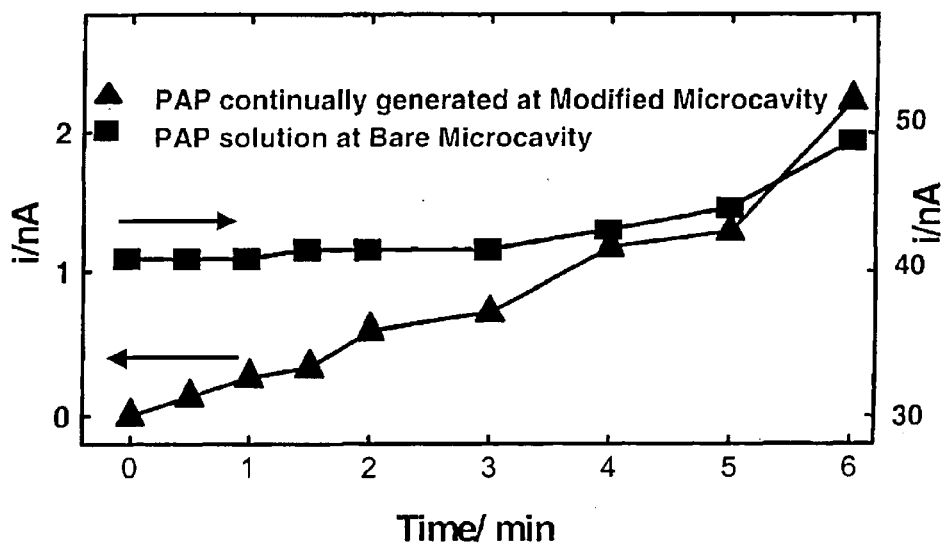
FIG. 23. The effect of evaporation on the CV signal at 50 mV/s of a modified microcavity (100 ng/mL IgG) using 200 nL of 4 mM PAPP in 0.1 M Tris, pH 9.0, (triangles) compared to that of a bare microcavity in 4 mM PAPR (squares). The experiments were carried out in a sealed humid environment to minimize evaporation using the same microcavity before and after modification.

The effect of evaporation vs. enzymatic generation. The concentration of species in the small volumes used throughout the immunoassay studies will change significantly due to evaporation of solvent if precautions are not taken. All steps involving small drops were performed in a sealed, water-saturated environment, with the exception of those involving the PAPP drop and electrochemical analysis. In the latter case, evaporation still plays a role to some extent, because the humid environment was not completely sealed due to an opening that accommodated the edge connector leads. In order to identify the time limit within which electrochemical analysis on 200 nL PAPP solutions should be completed, studies on the effect of evaporation were performed. Because current is proportional to the localized concentration at the detecting electrode, the plateau current of the CV responses of a solution containing a redox species can be used to follow the concentrating effect. FIG. 23 shows how the CV plateau current for PAPR changes with time at a modified microcavity and at a bare microcavity. That for the bare microcavity is constant for about 3 min. After 3 min, and especially noticeable at 5 min, the current rises, presumably due to the concentrating effect of evaporation. There is also a noticeable increase after 3 min, and especially at 5 min for the enzymatically-generated PAPR at the modified microcavity. Consequently, the increase in current in the first 3 min at the modified microcavity must be due to the turnover of PAPP to PAPR by the enzyme and not due to evaporation of water. Therefore, times less than 3 min should be selected when using 200 nL volumes under our conditions, so that determination of detection limit and sensitivity is accurate. The 200 nL drops evaluated at 2 min should be well inside this evaporation limit. Larger drops should show slower concentrating effects due to evaporation.

Figure 24:
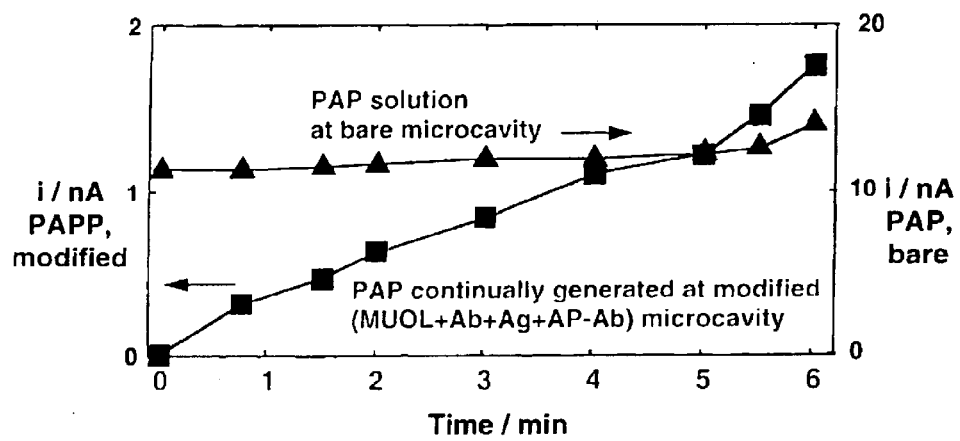
FIG. 24. The effect of evaporation on the CV signal of a modified microcavity in 0.5 L of 4 mM PAPP in 0.1 M Tris, pH 9.0, (triangles) compared to that of a bare microcavity in 4 mM $PAP_R$ (squares). The experiments were carried out in a humid environment to minimize evaporation. The increase in signal for the modified cavity for the first 5 min is due to generation of $PAP_R$ from PAPP by alkaline phosphatase. After 5 min, evaporation begins to play a role in the increase in signal.

FIG. 23 also illustrates the rate at which the PAPR concentration builds up near the detecting electrode. The CV response obtained in the 4 mM PAPR solution at the bare microcavity is that which would be expected if all of the 4 mM PAPP solution were converted to PAPR by the immobilized alkaline phosphatase at the modified microcavity. After 3 min, the current at the modified microcavity is about 2.15% of that of the bare microcavity based on the signal generated by two chips modified with 100 ng/mL Ag. This leads us to believe that even smaller volumes of PAPP, assuming evaporation is not an issue, should provide even faster increases in signal due to PAPR production, because the loss due to diffusion outside the microcavity is minimized. Studies on the effect of evaporation were performed on 0.5 L solution of $PAP_R$ in a humid environment. FIG. 24 shows how the CV signal changes with time at a modified microcavity and at a bare microcavity. That for the bare microcavity is constant over about 5 min. After 5 min, the current begins to rise, presumably due to concentration of the $PAP_R$. The percent rise in current after 5 min at the modified microcavity and the bare microcavity are the same. Consequently, the increase in current in the first 5 min at the modified microcavity must be due to the turnover of PAPP to $PAP_R$ by the enzyme and not due to evaporation of water. Therefore, results for detection limit and sensitivity at small volumes at microcavity devices for times near 5 min or less are not influenced significantly by evaporation.

FIG. 24 also illustrates how quickly the $PAP_R$ concentration builds up near the detecting electrode. After only 5 min, about 1/10 of the total concentration of PAPP can be detected in the form of $PAP_R$, providing a significant signal. Smaller volumes of PAPP should provide even faster increases in signal due to $PAP_R$ production, because the loss due to diffusion outside the microcavity is minimized.

Whereas, the present invention has been described in relation to the drawings attached hereto, it should be understood that other and further modifications, apart from those shown or suggested herein, may be made within the spirit and scope of this invention.

Bibliography (1) Niwa, O.; Halsall, H. B.; Heineman, W. R. *Anal. Chem.* 1993, 65, 1559–1563.
(2) Chen, T. K.; Luo, G.; Ewing, A. G. *Anal. Chem.* 1994, 66, 3031–3035.
(3) Bousse, L. *Sensors and Actuators B* 1996, 34, 270–275.
(4) Konig, A.; Reul, T.; Harmeling, C.; Spener, F.; Knoll, M.; Zaborosch, C. *Anal. Chem.* 2000, 72, 2022–2028.
(5) Kaneki, N.; Xu, Y.; Kumari, A.; Halsall, H. B.; Heineman, W. R.; Kissinger, P. *Anal. Chim. Acta* 1994, 287, 253–258.
(6) Moore, T. J.; Joseph, M. J.; Allen, B. W.; Coury, J., L. A. *Anal. Chem.* 1995, 67, 1896–1902.
(7) Perez, F. G.; Mascini, M. T.; Ibtisam E.; Turner, A. P. F. *Anal. Chem.* 1998, 70, 2380–2386.
(8) Sadik, O.; Van Emon, J. M. *Biosensors & Bioelectronics* 1996, 11, i–xi.
(9) Abdel Hamid, I.; Ivnitski, D.; Atanasov, P.; Wilkins, E. *Anal. Chim. Acta* 1999, 399, 99–108.
(10) Karyakin, A. A.; Karyakina, E. E.; Gorton, L. *Anal. Chem.* 2000, 72, 1720–1723.
(11) Xu, Y.; Halsall, H. B.; Heineman, W. R. *Journal of Pharmaceutical & Biomedical Analysis* 1989, 7, 1301–1311.
(12) Brewster, J. D.; Gehring, A. G.; Masenko, R. S.; Van Houten, L. J.; Crawford, C. J. *Anal. Chem.* 1996, 68, 4153–4159.
(13) Brooks, J. L.; Mirhabibollahi, B.; Kroll, R. G. *Applied and Environmental Microbiology* 1990, 56, 3278–3284.
(14) Clark, M. E.; Ingram, J. L.; Blakely, E. E.; Bowyer, W. J. *Journal of Electroanalytical Chemistry* 1995, 385, 157–162.
(15) Cousino, M. A.; Jarbawi, T. B.; Halsall, H. B.; Heineman, W. R. *Anal. Chem.* 1997, 545A–549A.
(16) Dong, Y.; Shannon, C. *Anal. Chem.* 2000, 72, 2371–2376.
(17) Grosvenor, A. L.; Feltus, A.; Conover, R. C.; Daunert, S.; Anderson, K. W. *Anal. Chem.* 2000, 72, 2590–2594.
(18) Rowe, C.; Leonard, T.; Feldstein, M.; Golden, P. J.; Scruggs, S.; MacCraith, B. D.; Cras, J.; Ligler, F. *Anal. Chem.* 1999, 71, 3846–3852.
(19) Horacek, J.; Skladal, P. *Anal. Chim. Acta* 1997, 347, 43–50.
(20) Scheller, F.; Schubert, F. *Biosensors;* Elsevier Publishers B.V.: Amsterdam, 1992.
(21) Heineman, W. R.; Halsall, H. B. *Anal. Chem.* 1985, 57, 1321A–1331A.
(22) Tothill, I. E.; Turner, A. P. F. *BIOSENSORS: New developments and opportunities in the diagnosis of livestock and diseases;* IAEA: Vienna, 1998.
(23) Turner, A. P. F.; Newman, J. D. In *Biosensors for Food Analysis;* Scott, A. O., Ed.; The Royal Society of Chemistry: Cambridge, 1998.
(24) Jenkins, S. H.; Halsall, H. B.; Heineman, W. R. *J. Clin. Immunoassay* 1990, 13, 99–104.
(25) Halsall, H. B.; Heineman, W. R.; Jenkins, S. H. *Clinical Chemistry* 1988, 34, 1701–1702.
(26) Thevenot, D. R.; Toth, K.; Durst, R. A.; Wilson, G. S. *Biosensors and Bioelectronics* 2001, 16, 121–131.
(27) Janata, J.; Josowicz, M.; Vanysek, P.; DeVaney, D. M. *Anal. Chem.* 1998, 70, 179R–208R.
(28) Bauer, C. G.; Eremenko, A. V.; Ehrentreich-Forster, E.; Bier, F. F.; Makower, A.; Halsall, H. B.; Heineman, W. R.; Scheller, F. W. *Anal. Chem.* 1996, 68, 2453–2458.
(29) Cheng, S. B.; Skinner, C. D.; Taylor, J.; Attiya, S.; Lee, W. E.; Picelli, G.; Harrison, D. J. *Anal. Chem.* 2001, 73, 1472–1479.
(30) Chiem, N.; Harrison, D. J. *Anal. Chem.* 1997, 69, 373–378.
(31) Koutny, L. B.; Schmalzing, D.; Taylor, T. A.; Fuchs, M. *Anal. Chem.* 1996, 68, 18–22.
(32) Tao, L.; Kennedy, R. T. *Anal. Chem.* 1996, 68, 3899–3906.
(33) Bratten, C. D. T.; Cobbold, P. H.; Cooper, J. M. *Chem. Commun.* 1998, 471–472.
(34) Dodge, A.; Fluri, K.; Verpoorte, E.; de Rooij, N. F. *Anal. Chem.* 2001, 73, 3400–3409.
(35) Kasai, S.; Yokota, A.; Zhou, H.; Nishizawa, M.; Niwa, K.; Onouchi, T.; Matsue, T. *Anal. Chem.* 2000, 72, 5761–5765.
(36) Shiku, H.; Matsue, T.; Uchida, I. *Anal. Chem.* 1996, 68, 1276–1278.
(37) Shiku, H.; Hara, Y.; Matsue, T.; Uchida, I.; Yamauchi, T. *J. Electroanal. Chem.* 1997, 438, 187–190.
(38) Wijayawardhana, C. A.; Wittstock, G.; Halsall, H. B.; Heineman, W. R. *Anal. Chem.* 2000, 72, 333–338.
(39) Henry, C.; Fritsch, I. *Anal. Chem.* 1999, 71, 550–556.
(40) Henry, C.; Fritsch, I. *Journal of the Electrochemical Society* 1999, 3367–3373.
(41) Foulds, N. C.; Frew, J. E.; Green, M. J. In *Biosensors A practical Approach;* Cass, A. E., Ed.; IRL Press, Oxford University: Oxford, 1990, pp 97–124.
(42) Huerta, F.; Morallon, E.; Vazquez, J. L.; Aldaz, A. *Journal of Electroanalytical Chemistry* 1999, 475, 38–45.
(43) Jiang, L.; Glidle, A.; Griffith, A.; McNeil, C. J.; Cooper, J. M. *Bioelecrochemistry and Bioenergetics* 1997, 15–23.
(44) Wang, J. *Anal. Chim. Acta* 1999, 399, 21–27.
(45) Fernandez-Sanchez, C.; Costa-Garcia, A. *Biosensors & Bioelectronics* 1997, 12, 403–413.
(46) Thompson, R. Q.; Porter, M.; Stuver, C.; Halsall, H. B.; Heineman, W. R.; Buckley, E.; Smyth, M. R. *Anal. Chim. Acta* 1993, 271, 223–229.
(47) Wijayawardhana, C. A.; Halsall, H. B.; Heineman, W. R. *Anal. Chim. Acta* 1999, 399, 3–11.
(48) Bratten, C. D. T.; Cobbold, P. H.; Cooper, J. M. *Anal. Chem.* 1997, 69, 253–258.
(49) Clark, R. A.; Hietpas, P. B.; Ewing, A. G. *Anal. Chem.* 1997, 69, 259–263.
(50) Abad-Villar, E. M.; Fernandez-Abedul, M. T.; Costa-Garcia, A. *Anal. Chim. Acta* 2000, 409, 149–158.
(51) La Salle, A. L. G.; Limoges, B.; Degrand, C. *Anal. Chem.* 1995, 67, 1245–1253.
(52) Malem, F.; Mandler, D. *Anal. Chem.* 1993, 65, 37–41.
(53) Ogura, K.; Kobayashi, M.; Nakayama, M.; Miho, Y. *Journal of Electroanalytical Chemistry* 1998, 449, 101–109.
(54) Tang, H. T.; Lunte, C. E.; Halsall, H. B.; Heineman, W. R. *Anal. Chim. Acta* 1988, 214, 187–195.
(55) Niwa, O.; Morita, M.; Tabei, H. *Electroanalysis* 1994, 6, 237–243.
(56) Peng, W.; Wang, E. *Anal. Chim. Acta* 1993, 281, 663–671.
(57) Wang, J.; Tian, B.; Rogers, K. R. *Anal. Chem.* 1998, 70, 1682–1685.
(58) Situmorang, M.; T., L. M.; Witzeman, K.; Heineman, W. R. *J. Chem. Ed* 1998, 75, 1035–1038.
(59) Gooding, J.; Hibbert, D. B. *Trends in Analytical Chemistry* 1999, 18, 525–533.
(60) Zull, J. E.; Reed-Mundell, J.; Lee, Y. W.; Vezenov, D.; Ziats, N. P.; Anderson, J. M.; Sukenik, C. N. *Journal of Industrial Microbiology* 1994, 13, 137–143.
(61) Browning-Kelley, M. E.; Wadu-Mesthrige, K.; Hari, V.; Liu, G. Y. *Langmuir* 1997, 13, 343–350.
(62) Cooper, E.; Legget, G. J. *Langmuir* 1998, 14, 4795–4801.

(63) Bain, C. D.; Troughton, E. B.; Tao, Y.; Evall, J.; Whitesides, G. M.; Nuzzo, R. G. *J. Am. Chem. Soc.* 1989, 111, 321–335.
(64) Hutt, D. A.; Legget, G. J. *J. Phys. Chem.* 1996, 100, 6657–6662.
(65) Mrksich, M.; Whitesides, G. M. *Annu. Rev. Biophys. Biomol. Struct.* 1996, 25, 55–78.
(66) DeRiemer, L. H.; Meares, C. F. *Biochemistry* 1981, 20, 1606–1612.
(67) Everett, R.; Fritsch-Faules, I. *Anal. Chim. Acta* 1995, 307, 253–268.
(68) Tender, L. M.; Worley, R. L.; Fan, H.; Lopez, G. P. *Langmuir* 1996, 12, 5515–5518.
(69) Widrig, C. A.; Chung, C.; Porter, M. D. *J. Electroanal. Chem.* 1991, 310, 335–359.
(70) Everett, W. R.; Welch, T. L.; Reed, L.; Fritsch-Faules, I. *Anal. Chem.* 1995, 67, 292–298.
(71) Terrill, R. H.; Balss, K. M.; Zhang, Y.; Bohn, P. W. *J. Am. Chem. Soc.* 2000, 122, 988–989.
(72) Walzcak, M. M.; Popenoe, D. D.; Deinhammer, R. S.; Lamp, B. D.; Chung, C.; Porter, M. D. *Langmuir* 1991, 7, 2687–2693.
(73) Weisshaar, D. E.; Lamp, B. D.; Porter, M. D. *J. Am. Chem. Soc.* 1992.
(74) Gong, W.; Elitzin, V. I.; Janardhanam, S.; Wilkins, C. L.; Fritsch, I. *J. Am. Chem. Soc.* 2001, 123, 769–770.
(75) Norrod, K. L.; Rowlen, K. L. *J. Am. Chem. Soc.* 1998, 120, 2656–2657.
(76) Schoenfish, M. H.; Pemberton, J. E. *J. Am. Chem. Soc.* 1998, 120, 4502–4513.
(77) Scott, J. R.; Baker, L. S.; Everett, W. R.; Wilkins, C. L.; Fritsch, I. *Anal. Chem.* 1997, 69, 2636–2639.
(78) Zhang, Y.; Terrill, R. H.; Tanzer, T. A.; Bohn, P. W. *J. Am. Chem. Soc.* 1998, 120, 2654–2655.
(79) Butler, J. E. *Immunochemistry of Solid Phase Immunoassay*, First ed.; CRC Press: Boca Raton, 1991.
(80) Delamarche, E.; Sundarababu, G.; Biebuyck, H.; Michel, B.; Gerber, C.; Sigrist, H.; Wolf, H.; Ringsdorf, H.; Xanthopoulos, N.; Mathieu, H. J. *Langmuir* 1996, 12, 1997–2006.
(81) Duan, C.; Meyerhoff, M. E. *Anal. Chem.* 1994, 66, 1369–1377.
(82) Sato, H.; Tomiyama, T.; Morimoto, H.; Nakajima, A. In *Proteins at Interfaces: Physiscochemical and Biochemical Studies;* American Chemical Society: Washington, D.C., 1987; Vol. 343, pp 76–87.
(83) Woodbury, R. G.; Wendin, C.; Clendenning, J.; Melendez, J.; Elkind, J.; Bartholomew, D.; Brown, S.; Furlong, C. E. *Biosensors & Bioelectronics* 1998, 13, 1117–1126.
(84) Kidoaki, S.; Matsuda, T. *Langmuir* 1999, 15, 7639–7646.
(85) Patel, N.; Davies, M. C.; Hartshorne, M.; Heaton, R. J.; Roberts, C. J.; Tendler, S. J. B.; Williams, P. M. *Langmuir* 1997, 13, 6485–6490.
(86) Schouten, S.; Stroeve, P.; Longo, M. L. *Langmuir* 1999, 15, 8133–8139.
(87) Su, X.; Chew, F. K.; Li, S. F. Y. *Analytical Biochemistry* 1999, 273, 66–72.
(88) Mrksich, M.; Sigal, G. B.; Whitesides, G. M. *Langmuir* 1995, 11, 4383–4385.
(89) Prime, K. L.; Whitesides, G. M. *J. Am. Chem. Soc.* 1993, 115, 10714–10721.
(90) Porter, M. D.; Bright, B. T.; Allara, D. L.; Chidsey, C. E. D. *J. Am. Chem. Soc.* 1987, 109, 3559–3568.
(91) Pretsch, E.; Simon, W.; Seibl, J.; Clerc, T. *Tables of spetral data for structure determinations of Organic compounds,* second ed.; Springer-Verlag: Berlin, 1989.
(92) Pistorius, A. M. A. *Spectroscopy Europe* 1995, 7, 8–15.
(93) Buijs, J.; Norde, W. *Langmuir* 1996, 12, 1605–1613.
(94) Conley, R. T. *Infrared Spectroscopy;* Allyn and Bacon, Inc.: Boston, 1966.
(95) Rao, C. N. *Chemical Applications of Infrared spectroscopy;* Academic Press, Inc.: New York, 1963.
(96) Roche; http://www.biochem.roche.corn/pak-insert/133151a.pdf, 2001; Vol. 2001.
(97) Skoog, D. A.; Holler, F. J.; Nieman, T. A. *Principles of Instrumental Analysis;* Saunders College Publishing: Philadelphia, 1998.
(98) Szabo, A.; Cope, D., K.; Tallman, D. E.; Kovach, P. M.; Wightman, R. M. *J. Electroanal. Chem.* 1987, 217.
(99) Adams, R. N. *Electrochemistry at Solid Electrodes;* Marcel and Dekker, Inc.: New York, 1969.
(100) Engblom, S. O.; Cope, D. K.; Tallman, D. E. *J. Electroanal. Chem.* 1996, 406, 23–31.

What is claimed is:

1. A method for quantitating or detecting the presence or absence of an analyte comprising:

addition of a sample to a microassay structure having at least one electrode and an analyte binding material;

allowing an analyte in said sample to bind to said analyte binding material in said microassay structure;

rinsing said microassay structure such that said analyte remains bound to said analyte binding material while the remainder of said sample is removed;

addition of an analyte binding molecule having a carrier species attached wherein said carrier species includes an electroactive species capable of generating a current by either accepting or transmitting one or more electrons to the at least one electrode and wherein said carrier species may be activated such that it releases the electroactive species;

allowing said analyte binding molecule to bind to said analyte;

activating said carrier species wherein said activation of said carrier species is selected from the group consisting of change in temperature, change in pH, and addition of an activating compound; and, measuring a current through said microassay structure by means of the at least one electrode within the microassay structure thereby quantitating or detecting the presence or absence of the analyte.

2. The method of claim 1 wherein said carrier species is a metallo protein and the electroactive species is a metal ion.

3. The method of claim 1 wherein said carrier species is a metal ion carrying dendrimer and the electroactive species is a metal ion.

4. The method of claim 1 wherein said carrier species is selected from the group consisting of metallo-protein, dendrimer or chelating agents.

5. The method structure claim 1 wherein the microassay structure further comprises a microcavity having an opening and a lipid bilayer suspended across the opening of said microcavity.

6. The method of claim 1 wherein the analyte binding materials in said microassay structure is selected from the group consisting of a primary antibody, a polynucleotide, polystyrene, a self-assembled monolayer or a ligand.

7. The method of claim 1 wherein the analyte binding molecule is selected from the group consisting of a secondary antibody, a protein, or a ligand.

* * * * *

UNITED STATES PATENT AND TRADEMARK OFFICE
CERTIFICATE OF CORRECTION

PATENT NO. : 6,887,714 B2
DATED : May 3, 2005
INVENTOR(S) : Fritsch et al.

It is certified that error appears in the above-identified patent and that said Letters Patent is hereby corrected as shown below:

Title page,
Item [75], Inventors, "Robert Beittle, Jr." should be -- Robert R. Beitle, Jr. --.
Item [73], Assignee, "Little Rock, AK" should be -- Little Rock, AR --.

Column 28,
Line 55, "structure" should be -- of --.

Signed and Sealed this

Fourteenth Day of February, 2006

JON W. DUDAS
*Director of the United States Patent and Trademark Office*

UNITED STATES PATENT AND TRADEMARK OFFICE
Certificate

Patent No. 6,887,714 B2                                                         Patented: MaY 3, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Ingrid Fritsch, Fayetteville, AR (US); Robert Beittle, Jr. Fayetteville, AR (US); Zoraida Aguilar, Cincinnati, OH (US).

Signed and Sealed this TwentY-seventh Day of November 2007.

WILLIAM R. DIXON, JR.
*Special Program Examiner*
Technology Center 1600